US012639810B2

(12) United States Patent
Xu et al.

(10) Patent No.: US 12,639,810 B2
(45) Date of Patent: May 26, 2026

(54) IMAGE SCANNING METHODS AND SYSTEMS FOR MEDICAL DEVICES

(71) Applicant: SHANGHAI UNITED IMAGING HEALTHCARE CO., LTD., Shanghai (CN)

(72) Inventors: Tianyi Xu, Shanghai (CN); Xiaoyue Gu, Shanghai (CN); Shengguo Jia, Shanghai (CN); Jinlong Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 583 days.

(21) Appl. No.: 18/154,787

(22) Filed: Jan. 13, 2023

(65) Prior Publication Data

US 2023/0196573 A1 Jun. 22, 2023

Related U.S. Application Data

(63) Continuation of application No. PCT/CN2021/106049, filed on Jul. 13, 2021.

(30) Foreign Application Priority Data

Jul. 13, 2020 (CN) .......................... 202010667635.2
Aug. 27, 2020 (CN) .......................... 202010875666.7

(51) Int. Cl.
*G06T 7/00* (2017.01)
*A61B 6/04* (2006.01)
(Continued)

(52) U.S. Cl.
CPC .......... *G06T 7/0012* (2013.01); *A61B 6/0407* (2013.01); *G06T 7/11* (2017.01);
(Continued)

(58) Field of Classification Search
CPC . G06T 7/0012; G06T 7/11; G06T 7/70; G06T 2207/10081; G06T 2207/10104;
(Continued)

(56) References Cited

U.S. PATENT DOCUMENTS 11,354,831 B2 * 6/2022 Feng ...................... A61B 6/504
11,501,460 B2 * 11/2022 Rinck ........................ G06T 7/70
(Continued)

FOREIGN PATENT DOCUMENTS

CN        107789001 A     3/2018
CN        109567852 A     4/2019
(Continued)

OTHER PUBLICATIONS

The Extended European Search Report in European Application No. 21842094.1 mailed on Jun. 2, 2023, 7 pages.
(Continued)

*Primary Examiner* — Shefali D Goradia
(74) *Attorney, Agent, or Firm* — METIS IP LLC

(57) ABSTRACT

The present disclosure relates to an image scanning method and system for a medical device. The method may include determining a target position of a scanned object in a scanning region of the medical device; moving the scanned object to the target position. The method may include controlling the medical device to perform a scanning on the scanned object to obtain a scanned image of the scanned object. The method may include determining at least one abnormal point in the scanned image and recommending a scanning protocol based on the at least one abnormal point. The method may further include controlling the medical device to perform a scanning on the scanned object based on the scanning protocol.

16 Claims, 12 Drawing Sheets

100

(51) Int. Cl.

| | |
|---|---|
| *G06T 7/11* | (2017.01) |
| *G06T 7/70* | (2017.01) |
| *G06V 10/70* | (2022.01) |
| *G16H 30/20* | (2018.01) |

(52) U.S. Cl.

CPC ................ *G06T 7/70* (2017.01); *G06V 10/70* (2022.01); *G16H 30/20* (2018.01); *G06T 2207/10081* (2013.01); *G06T 2207/10104* (2013.01)

(58) Field of Classification Search

CPC ..... A61B 6/0407; A61B 5/0037; A61B 5/055; A61B 6/032; A61B 6/037; A61B 6/545; A61B 6/4417; G06V 10/70; G16H 30/20

See application file for complete search history.

(56) References Cited

U.S. PATENT DOCUMENTS

| | | | |
|---|---|---|---|
| 12,064,268 B2 * | 8/2024 | Li | A61B 5/1116 |
| 2010/0220909 A1 | 9/2010 | Thielemans et al. | |
| 2011/0317900 A1 | 12/2011 | Pal et al. | |
| 2013/0131493 A1 | 5/2013 | Wollenweber et al. | |
| 2013/0267829 A1 | 10/2013 | Ojha et al. | |
| 2015/0087974 A1 | 3/2015 | Black | |
| 2015/0119703 A1 | 4/2015 | Mitchell et al. | |
| 2018/0289340 A1 | 10/2018 | Trindade Rodrigues et al. | |

| | | | |
|---|---|---|---|
| 2020/0211208 A1 | 7/2020 | Wen et al. | |
| 2021/0158563 A1 * | 5/2021 | Rinck | G06T 7/70 |
| 2022/0399107 A1 * | 12/2022 | Shen | G16H 40/20 |

FOREIGN PATENT DOCUMENTS

| | | |
|---|---|---|
| CN | 109584322 A | 4/2019 |
| CN | 109692015 A | 4/2019 |
| CN | 109745066 A | 5/2019 |
| CN | 109924993 A | 6/2019 |
| CN | 109938764 A | 6/2019 |
| CN | 110415310 A | 11/2019 |
| CN | 110547819 A | 12/2019 |
| CN | 110960241 A | 4/2020 |
| CN | 111374690 A | 7/2020 |
| CN | 111887878 A | 11/2020 |
| CN | 111904379 A | 11/2020 |
| WO | 2019245622 A1 | 12/2019 |

OTHER PUBLICATIONS

International Search Report in PCT/CN2021/106049 mailed on Aug. 26, 2021, 8 pages.

Written Opinion in PCT/CN2021/106049 mailed on Aug. 26, 2021, 11 pages.

First Office Action in Chinese Application No. 202010875666.7 mailed on Jun. 9, 2022, 23 pages.

* cited by examiner

100

<u>200</u>

400

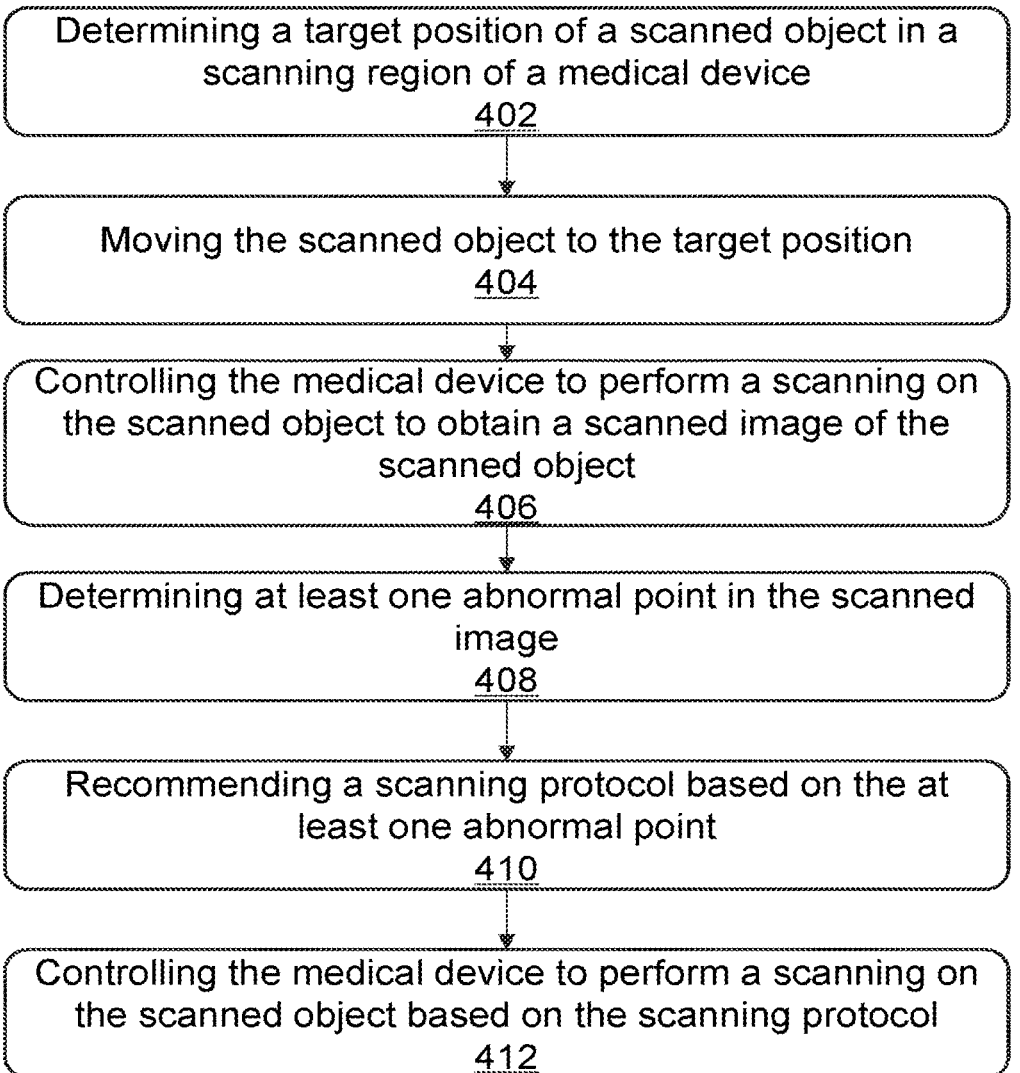

Determining a target position of a scanned object in a
scanning region of a medical device
402

Moving the scanned object to the target position
404

Controlling the medical device to perform a scanning on
the scanned object to obtain a scanned image of the
scanned object
406

Determining at least one abnormal point in the scanned
image
408

Recommending a scanning protocol based on the at
least one abnormal point
410

Controlling the medical device to perform a scanning on
the scanned object based on the scanning protocol
412

Determining scanning parameters
510

Determining, based on the scanning parameters,
a target position of a scanned object in a
scanning region of a medical device
520

Controlling a scanning couch to move the
scanned object to the target position
530

Controlling the medical device to perform a
scanning on the scanned object
540

<u>600</u>

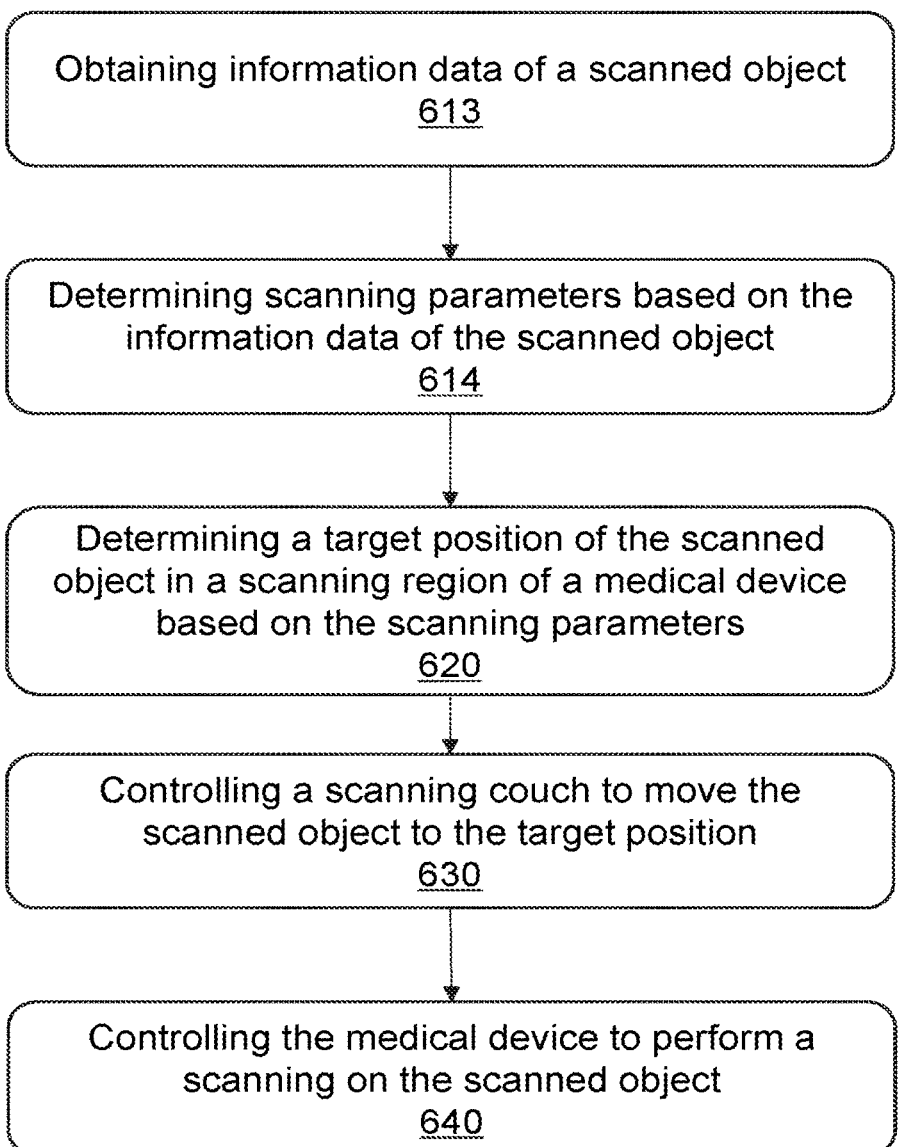

Obtaining information data of a scanned object
<u>613</u>

Determining scanning parameters based on the
information data of the scanned object
<u>614</u>

Determining a target position of the scanned
object in a scanning region of a medical device
based on the scanning parameters
<u>620</u>

Controlling a scanning couch to move the
scanned object to the target position
<u>630</u>

Controlling the medical device to perform a
scanning on the scanned object
<u>640</u>

FIG. 6

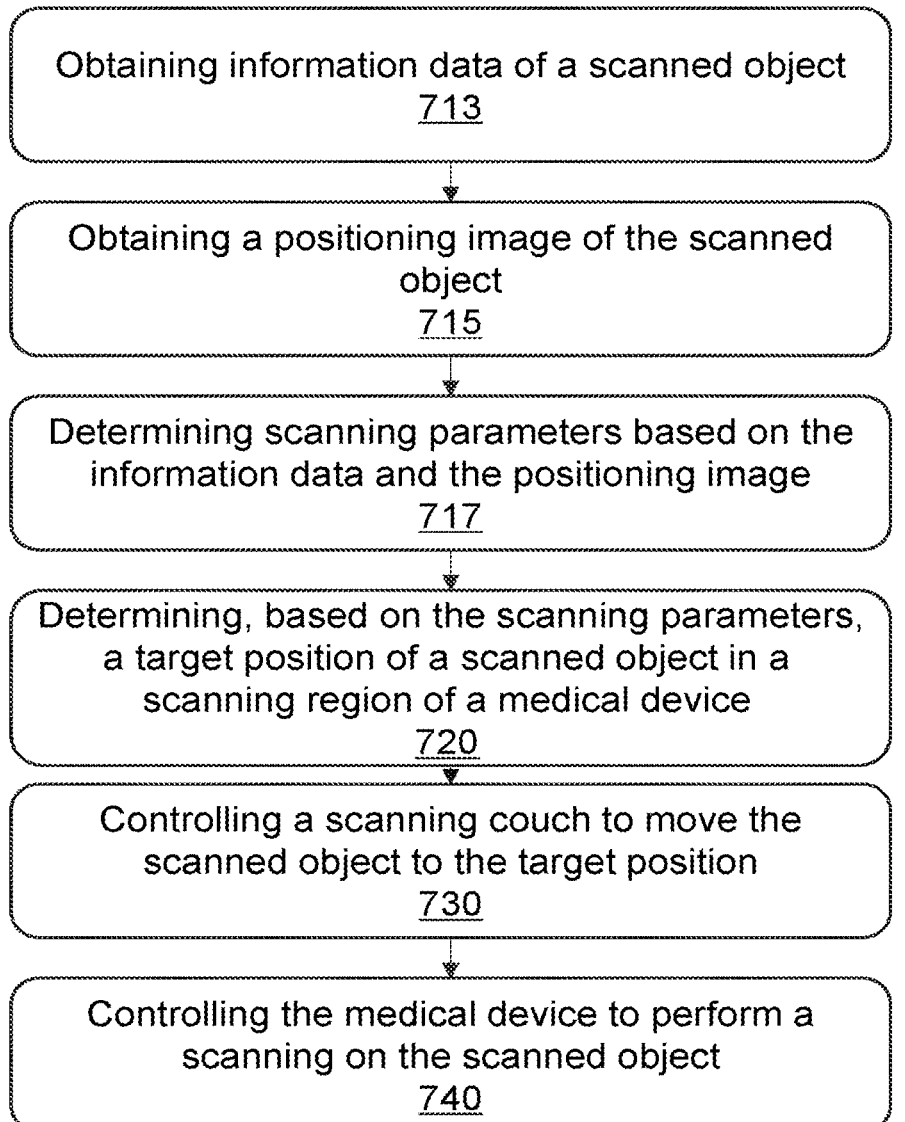

700

Obtaining information data of a scanned object
713

Obtaining a positioning image of the scanned object
715

Determining scanning parameters based on the information data and the positioning image
717

Determining, based on the scanning parameters, a target position of a scanned object in a scanning region of a medical device
720

Controlling a scanning couch to move the scanned object to the target position
730

Controlling the medical device to perform a scanning on the scanned object
740

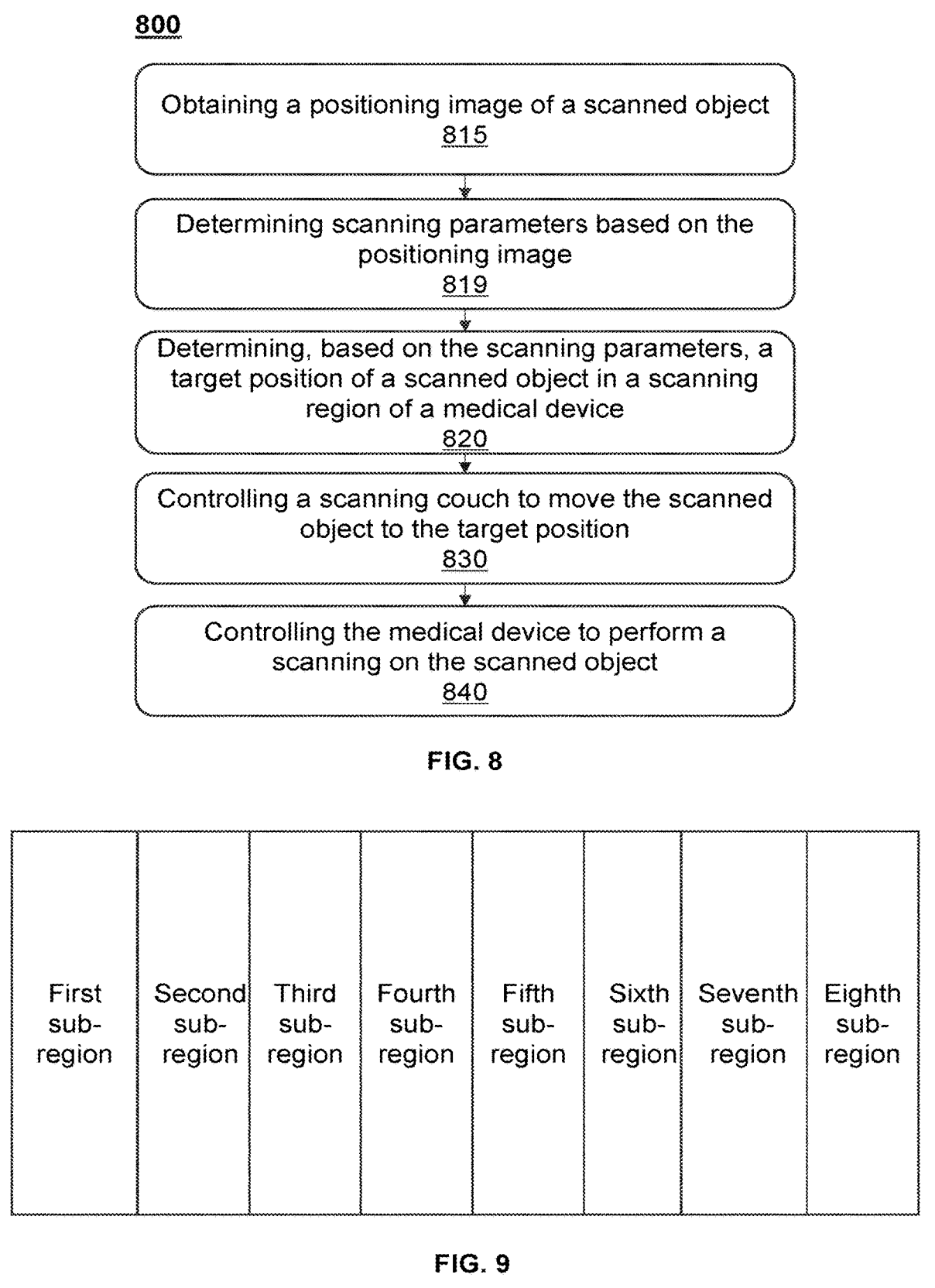

Obtaining a positioning image of a scanned object
815

Determining scanning parameters based on the
positioning image
819

Determining, based on the scanning parameters, a
target position of a scanned object in a scanning
region of a medical device
820

Controlling a scanning couch to move the scanned
object to the target position
830

Controlling the medical device to perform a
scanning on the scanned object
840

FIG. 8

| First sub-region | Second sub-region | Third sub-region | Fourth sub-region | Fifth sub-region | Sixth sub-region | Seventh sub-region | Eighth sub-region |
|---|---|---|---|---|---|---|---|

Figure 15:
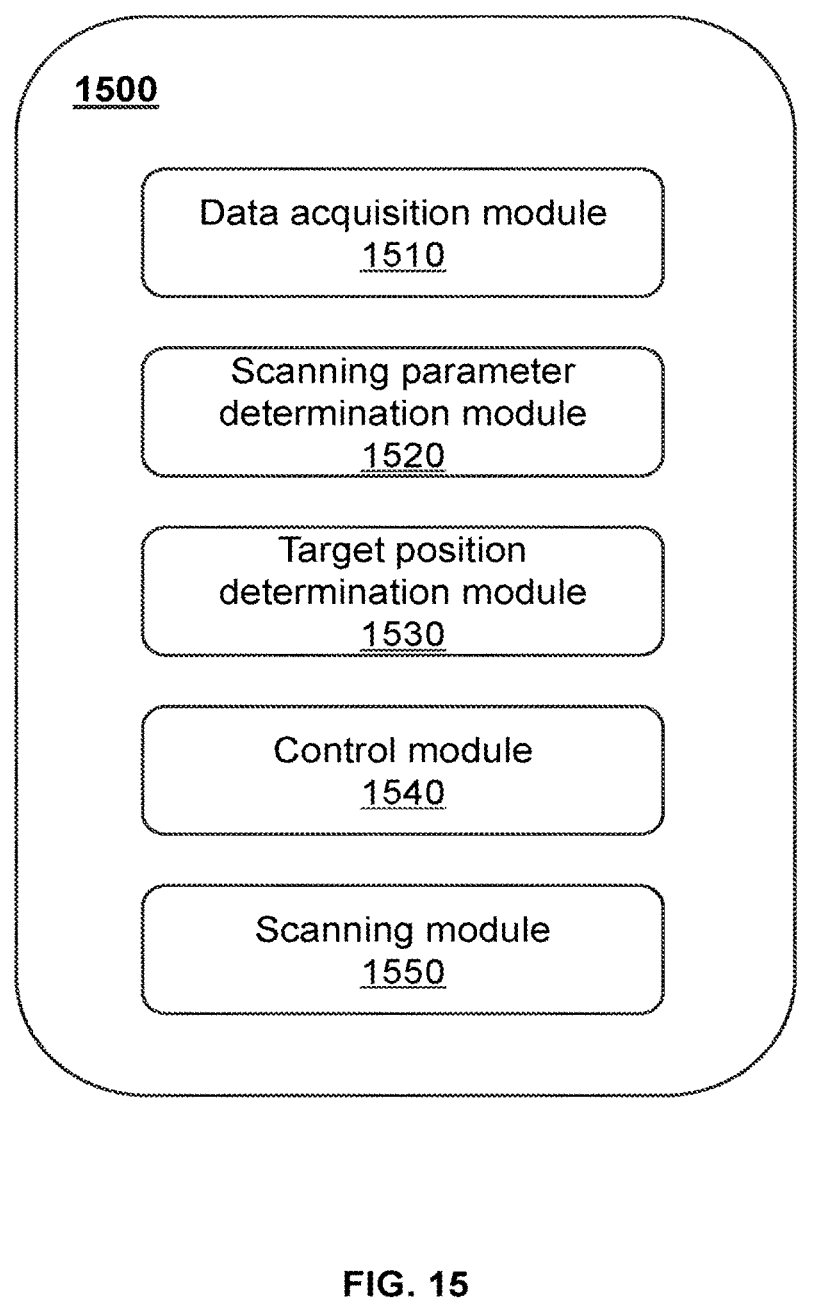

Data acquisition module
1510

Scanning parameter
determination module
1520

Target position
determination module
1530

Control module
1540

Scanning module
1550

IMAGE SCANNING METHODS AND SYSTEMS FOR MEDICAL DEVICES

CROSS-REFERENCE TO RELATED APPLICATIONS

This application is a Continuation of International Application No. PCT/CN2021/106049 filed on Jul. 13, 2021, which claims priority to Chinese Application No. 202010875666.7, filed on Aug. 27, 2020, and priority to Chinese Application No. 202010667635.2, filed on Jul. 13, 2020, the contents of each of which are hereby incorporated by reference to its entirety.

TECHNICAL FIELD

The present disclosure generally relates to the field of medical technology, and more particular, relates to an image scanning method, device, and storage medium for a medical device.

BACKGROUND

Imaging technology has been widely used in the fields of biological testing and medical diagnosis. Taking Positron Emission Computed Tomography (PET) as an example, a general method of PET imaging includes labeling a substance (generally necessary for biological life metabolism, e.g., glucose, protein, nucleic acid, fatty acid, etc.) with a short-lived radionuclide (e.g., F18, carbon 11, etc.), and injecting the labeled substance into the body, and then visualizing and measuring a metabolic activity of the labeled substance in the tissue, thereby providing information associated with the function of the tissue.

During a medical imaging process, it is often necessary to move a scanned object to a target position for scanning based on a planned scanning range. In addition, after a partial scanning result of a scanned subject is obtained, some other types of scanning may be performed on that scanned object due to clinical diagnostic needs. For example, during a PET scanning process, after the PET image is obtained, it may be necessary to further study the medical findings in the image to determine the need for further scanning of the medical findings.

Therefore, it is desired to provide an image scanning method for a medical device through which a targeted scanning operation can be automatically performed according to the actual conditions of the scanned object.

SUMMARY

An aspect of the present disclosure provides an image scanning method for a medical device. The method may include determining a target position of a scanned object in a scanning region of the medical device; moving the scanned object to the target position. The method may include controlling the medical device to perform a scanning on the scanned object to obtain a scanned image of the scanned object. The method may include determining at least one abnormal point in the scanned image and recommending a scanning protocol based on the at least one abnormal point. The method may further include controlling the medical device to perform a scanning on the scanned object based on the scanning protocol.

In some embodiments, the determining the target position of the scanned object in the scanning region of the medical device may include dividing the scanning region into a plurality of sub-regions based on a sensitivity distribution and/or geometrical structure parameters of the scanning region; and determining the target position of the scanned object in the scanning region of the medical device based on information data of the scanned object and an extent of the sub-regions.

In some embodiments, in response to that the scanned object is located at the target position, a target scanning site of the scanned object may be located in a high-sensitivity scanning region of the medical device.

In some embodiments, the medical device may include a PET scanner. The at least one abnormal point may include at least one glucose metabolism abnormal point.

In some embodiments, the determining the target position of the scanned object in the scanning region of the medical device may include determining a scanning range of the scanned object; determining a geometric center of the scanning range; and determining the target position based on the geometric center of the scanning range and a center of the scanning region of the medical device.

In some embodiments, the medical device may include a first modal imaging device and a second modal imaging device. The scanned image may be obtained by the first modal imaging device. The controlling the medical device to perform the scanning on the scanned object based on the scanning protocol may include controlling the second modal imaging device to perform a second scanning on the scanned object based on the scanning protocol to obtain a second scanned image of the scanned object.

In some embodiments, the first modal imaging device may include a PET scanner. The second modal imaging device may include a CT scanner.

A further aspect of the present disclosure provides a medical device for image scanning. The medical device may include a control device, a scanning couch, a scanner, and at least one processor. The control device may be configured to determine a target position of a scanned object in a scanning region of the scanner. The scanning couch may be configured to move the scanned object to the target position. The scanner may be configured to: perform a scanning on the scanned object to obtain a scanned image and perform a scanning on the scanned object based on a scanning protocol. The at least one processor may be configured to determine at least one abnormal point in the scanned image and recommend the scanning protocol based on the at least one abnormal point.

A still further aspect of the present disclosure provides an image scanning method for a medical device. The method may include determining scanning parameters; determining, based on the scanning parameters, a target position of a scanned object in a scanning region of the medical device; controlling a scanning couch to move the scanned object to the target position; and controlling the medical device to perform a scanning on the scanned object.

A still further aspect of the present disclosure provides an imaging device for image scanning. The medical device may include at least one processor, a control device, a scanning couch, and a scanner. The at least one processor may be configured to determine scanning parameters. The control device may be configured to determine a target position of a scanned object in a scanning region of the scanner based on the scanning parameters. The scanning couch may be configured to move the scanned object to the target position. The scanner may be configured to perform a scanning on the scanned object.

A still further aspect of the present disclosure provides an image scanning method for a medical device. The method may include obtaining a scanned image by causing the medical device to perform a scanning on a scanned object; determining at least one abnormal point in the scanned image; recommending a scanning protocol based on the at least one abnormal point; and controlling the medical device to perform a scanning on the scanned object based on the scanning protocol.

A still further aspect of the present disclosure provides an imaging device for image scanning. The medical device may include at least one processor and a scanner. The at least one processor may be configured to obtain a scanned image by causing the scanner to perform a scanning on a scanned object; determine at least one abnormal point in the scanned image; and recommend a scanning protocol based on the at least one abnormal point. The scanner may be configured to perform a scanning on the scanned object based on the scanning protocol.

In some embodiments, the scanner may include a first modal imaging device and a second modal imaging device. The first modal imaging device may include a PET scanner. The second modal imaging device may include a CT scanner.

A still further aspect of the present disclosure provides a computer device comprising a storage, a processor, and computer programs stored on the storage and runnable on the processor. When executing the computer programs, the processor may implement the image scanning method for the medical device as described above.

A still further aspect of the present disclosure provides a computer-readable storage medium including computer programs. When executing the computer programs, a processor may implement the image scanning method for the medical device as described above.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 4 is a flowchart illustrating an exemplary image scanning method according to some embodiments of the present disclosure;

FIG. 6 is a flowchart illustrating an exemplary image scanning method according to some embodiments of the present disclosure;

FIG. 7 is a flowchart illustrating an exemplary image scanning method according to some embodiments of the present disclosure;

FIG. 8 is a flowchart illustrating an exemplary image scanning method according to some embodiments of the present disclosure;

FIG. 9 is a schematic diagram illustrating exemplary scanning sub-regions according to some embodiments of the present disclosure;

FIG. 15 is a block diagram illustrating an exemplary image scanning device according to some embodiments of the present disclosure;

DETAILED DESCRIPTION

Figure 1:
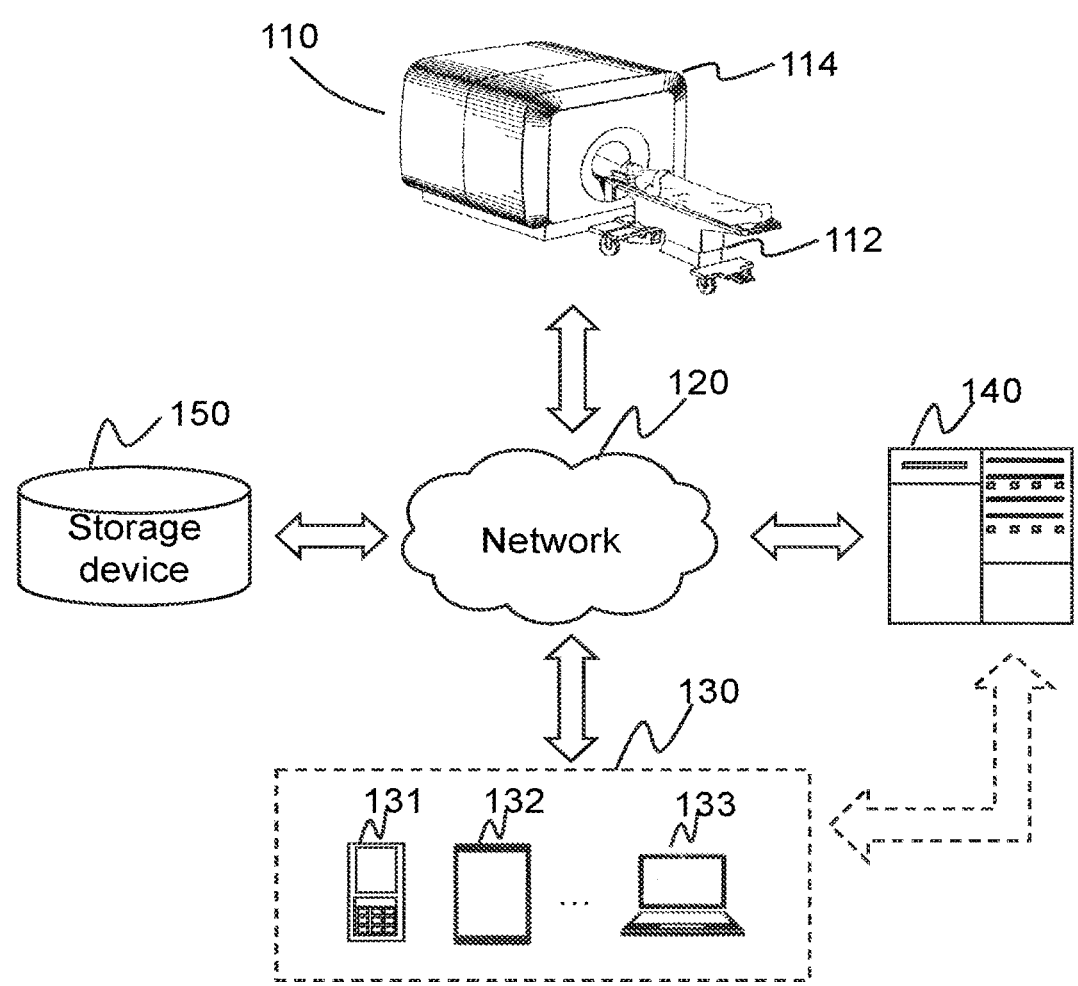
FIG. 1 is a schematic diagram illustrating an exemplary application scenario of a medical device according to some embodiments of the present disclosure.

In order to more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings. Unless obviously obtained from the context or the context illustrates otherwise, the same numeral in the drawings refers to the same structure or operation.

It should be understood that the "system," "device," "unit," and/or "module" used herein are one method to distinguish different components, elements, parts, sections, or assemblies of different levels. However, if other words can achieve the same purpose, the words can be replaced by other expressions.

As used in the disclosure and the appended claims, the singular forms "a," "an," and "the" include plural referents unless the content clearly dictates otherwise; the plural forms may be intended to include singular forms as well. In general, the terms "comprise," "comprises," and/or "comprising," "include," "includes," and/or "including," merely prompt to include steps and elements that have been clearly identified, and these steps and elements do not constitute an exclusive listing. The methods or devices may also include other steps or elements.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

In Positron Emission Computed Tomography (PET) imaging, a radionuclide is injected into the body of a target object (i.e., a scanned object) to cause a substance in the target object (generally a substance necessary for biological life metabolism, e.g., glucose, proteins, nucleic acids, fatty acids, etc.) to be labeled with a short-lived radionuclide (e.g., F18, carbon 11, etc.). In the body of the target object, the radionuclide releases positrons during decay, and one positron annihilates when it encounters an electron in its travels, resulting in a pair of photons of 511 keV energy in opposite directions. The photon signal may be captured by a high-sensitivity camera and corrected by a computer for scattering and random information. After the same analytical processing of different positrons, a three-dimensional image reflecting the aggregation of radionuclides in the target object may be obtained, thus providing information associated with a function of tissue. In some embodiments, during PET scanning, a system may move the scanned object to a corresponding position for scanning according to the planned scanning range. The same scanned object or different scanned objects may have different scanning positions in a PET scanner due to the different scanning ranges.

In some embodiments, medical imaging techniques may include computed tomography (CT), direct digital radiography (DR), magnetic resonance imaging (MRI), or the like. In the medical imaging, scanning images may be obtained by selecting one or more scanning protocols. In some embodiments, during scanning, the scanned object may be scanned again according to some other types of scanning protocols due to clinical diagnosis after partial scanning results have been obtained. For example, after a sagittal or coronal scanning of the spine, some abnormal lesions are found, and some information about the spine is wanted to be further scrutinized and a more detailed cross-sectional scanning of the intervertebral disc or vertebral body is desired. At this time, the scanning protocol corresponding to the cross-sectional position needs to be selected and added to the list for scanning. As another example, during a PET scanning, after a PET image is obtained, further research may be required on the medical findings in the image, thereby creating a need for further scanning of the medical finding.

Embodiments of the present disclosure provide an image scanning method for a medical device. The image scanning method may include determining a target position of a scanned object in a scanning region of the medical device based on scanning parameters of the scanned object before performing a scanning on the scanned object, moving the scanned object to the target position, and performing a scanning on the scanned object. The image scanning method may further include after obtaining a scanned image of the scanned object, determining abnormal points in the scanned image, recommending a scanning protocol based on the abnormal points, and performing a scanning on the scanned object based on the scanning protocol confirmed by a user based on the recommended scanning protocol.

FIG. 1 is a schematic diagram illustrating an exemplary application scenario of a medical device according to some embodiments of the present disclosure.

As shown in FIG. 1, in some embodiments, the system 100 may include a medical device 110, a network 120, a terminal device 130, a processing device 140, and a storage device 150. A plurality of components of the system 100 may be connected to each other via the network 120. For example, the medical device 110 and the terminal device 130 may be connected or in communication via the network 120. As another example, the medical device 110 and the processing device 140 may be connected or in communication via the network 120.

The medical device 110 may be configured to scan a scanned object within a detection region or a scanning region to obtain scanning data of the scanned object. In some embodiments, the scanned object may include a biological object and/or a non-biological object. For example, the scanned object may be animate or inanimate organic and/or inorganic matter.

In some embodiments, the medical device 110 may be a non-invasive imaging device for disease diagnosis or research purposes. For example, the medical device 110 may include a single modality scanner and/or a multi-modality scanner. The single modality scanner may include, for example, an ultrasound scanner, an x-ray scanner, a computed tomography (CT) scanner, a magnetic resonance imaging (MRI) scanner, an ultrasonograph, a positron emission computed tomography (PET) scanner, an optical coherence tomography (OCT) scanner, an ultrasound (US) scanner, an intravascular ultrasound (IVUS) scanner, a near infrared spectroscopy (NIRS) scanner, far infrared (FIR) scanner, or the like, or any combination thereof. The multi-modality scanner may include, for example, an X-ray-MRI scanner, a PET-X-ray scanner, a single photon emission computed tomography-MRI (SPECT-MRI) scanner, PET-CT scanner, a digital subtraction angiography-MRI (DSA-MRI) scanner, etc. The above description of the scanners is merely provided for the purposes of illustration, and not intended to limit the scope of this present disclosure. As used herein, the term "imaging modality" or "modality" broadly refers to an imaging method or technique for collecting, generating, processing, and/or analyzing imaging information of a target object.

In some embodiments, the medical device 110 may determine scanning parameters based on information data and/or a positioning image of a scanned object, and determine a target position of the scanned object in a scanning region of the medical device based on the scanning parameters. In some embodiments, the medical device 110 may determine at least one abnormal point in the scanned image, and recommend a scanning protocol based on the at least one abnormal point.

In some embodiments, the medical device 110 may include a module and/or a component configured to perform a scanning and/or associated analysis. For example, the medical device 110 may include a control device, a scanning couch (e.g., a scanning couch 112), a scanner (e.g., a scanner 114), and at least one processor (e.g., the processing device 140), etc. The control device (not shown in the figure) may be configured to determine a target position of a scanned object in a scanning region of the scanner. In some embodiments, the medical device may include an interactive interface. The control device may obtain information input by a user through the interactive interface to determine the target position of the scanned object in the scanning region of the scanner based on the information. In some embodiments, the control device may communicate with the terminal device 130 to obtain the information input by the user through the interactive interface of the terminal device 130, and determine the target position of the scanned object in the scanning region of the scanner based on the information. For example, the user may select and determine a scanning range and/or positional manner of the scanned object by dragging a scanning box on the interactive interface of the terminal device 130 or the medical device 110. The control device may determine the target position of the scanned object in the scanning region of the scanner based on a position of the scanning box. The scanning box may reflect a range of the scanning region that covers the scanned object when the scanner performs a scanning on the scanned object. In some embodiments, the control device may automatically determine the target position of the scanned object in the scanning region of the scanner based on the scanning parameters and/or positioning image. For example, the control device may obtain, from the processing device 140, the target position of the scanned object in the scanning region of the scanner that is determined by the processing device 140 based on the scanning parameters. In some embodiments, the control device may be configured to control one or more components of the medical device 110. For example, the control device may obtain, from the interactive interface, an instruction that is manually input by the user and control the scanner 114 to perform a scanning on the scanned object based on the instruction. As another example, the control device may control the scanning couch 112 to move the scanned object to the target position in the scanning region of the scanner 114 based on a scanning couch motion control instruction determined by the processing device 140. In some embodiments, the control device and a control module 330 in an image scanning system 300 may be modules with the same structure and/or function.

The scanning couch may be configured to support a scanned object. In some embodiments, the scanning couch may include a driver. The scanning couch may be driven by the driver. For example, a couch plate and/or a drive wheel of the scanning couch may move to move the scanned object placed on the scanning couch to the target position.

The scanner may be configured to perform a scanning on the scanned object within the scanning region. In some embodiments, the scanner may include a PET scanner, a CT scanner, an MR scanner, etc. In some embodiments, the processing device 140 may be configured to determine scanning parameters, abnormal points in the scanned image, recommended scanning protocols, etc. In some embodiments, the processing device 140 may be configured to determine the target position of the scanned object in the scanning region of the scanner. More descriptions regarding the image scanning of the medical device may be found elsewhere in the present disclosure (e.g., FIGS. 4-7 and the description thereof).

In some embodiments, data obtained by the medical device 110 (e.g., the scanning data and the scanning image of the scanned object, etc.) may be transmitted to the processing device 140 for further analysis. Additionally or alternatively, the data obtained by the medical device 110 may be sent to a terminal device (e.g., the terminal device 130) for display and/or a storage device (e.g., the storage device 150) for storage.

The network 120 may include any network capable of facilitating the exchange of information and/or data of the system 100. In some embodiments, at least one component of system 100 (e.g., the medical device 110, the terminal device 130, the processing device 140, the storage device 150) may exchange information and/or data with at least one other component of the system 100 via network 120. For example, the processing device 140 may obtain the scanning data or the scanned image of the scanned object from the medical device 110 via the network 120. The network 120 may include a public network (e.g., Internet), a private network (e.g., a local area network (LAN)), a wired network, a wireless network (e.g., an 802.11 network, a Wi-Fi network), a frame relay network, a virtual private network (VPN), a satellite network, a telephone network, a router, a hub, a switch, a fiber optic network, a telecommunications network, an Intranet, a wireless local area network (WLAN), a metropolitan area network (MAN), a public switched telephone network (PSTN), a Bluetooth™ network, a Zig-Bee™ network, a near field communication (NFC) network, or any combination thereof. In some embodiments, the network 120 may include at least one network access point. For example, the network 120 may include a wired and/or wireless network access point, such as a base station and/or an internet exchange point, and at least one component of the system 100 may connect to the network 120 via the access point to exchange data and/or information.

The terminal device 130 may be in communication and/or connection with the medical device 110, the processing device 140, and/or the storage device 150. For example, the user may interact with the medical device 110 through the terminal device 130 to control one or more components of the medical device 110. In some embodiments, the terminal device 130 may include a mobile device 131, a tablet computer 132, a laptop computer 133, or the like, or any combination thereof. For example, the mobile device 131 may include a mobile control handle, a personal digital assistant (PDA), a smartphone, or the like, or any combination thereof.

In some embodiments, the terminal device 130 may include an input device, an output device, or the like. The input device may be a keyboard input, a touch screen (e.g., with tactile or tactile feedback) input, a voice input, an eye-tracking input, a gesture-tracking input, a brain monitoring system input, an image input, a video input, or any other similar input mechanism. The input information received via the input device may be transmitted to the processing device 140, via, for example, a bus, for further processing. Other types of the input device may include a cursor control device, for example, a mouse, a trackball, a cursor direction key, or the like. In some embodiments, an operator (e.g., a medical staff) may input a scanning instruction (e.g., a scanning protocol, a scanning range, a scanning execution, etc.), etc. via the input device. The output device may include a display, a speaker, a printer, or the like, or any combination thereof. In some embodiments, the output device may be configured to output an image (e.g., a scanned image, a photographic image, etc.) of the scanned object obtained by the medical device 110, and/or abnormal points in the scanned image determined by the processing device 140, etc. In some embodiments, the terminal device 130 may be part of the processing device 140.

The processing device 140 may process data and/or information obtained from the medical device 110, the at least one terminal device 130, the storage device 150, or other components of the system 100. For example, the processing device 140 may obtain, from the medical device 110, analyze, and process a tomography image, a PET scan image, etc. In some embodiments, the processing device 140 may be a single server or a group of servers. The group of servers may be centralized or distributed. In some embodiments, the processing device 140 may be local or remote. For example, the processing device 140 may access information and/or data from the medical device 110, the at least one terminal device 130, and/or the storage device 150 via the network 120. As another example, the processing device 140 may connect directly to the medical device 110, the at least one terminal device 130, and/or the storage device 150 to access the information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or any combination thereof.

In some embodiments, the processing device 140 may include one or more processors (e.g., a single-chip processor or a multi-chip processor). Merely by way of example, the processing device 140 may include a central processing unit (CPU), a specialized integrated circuit (ASIC), a specialized instruction set processor (ASIP), an image processing unit (GPU), a physical computing processing unit (PPU), a digital signal processor (DSP), a field programmable gate array (FPGA), a programmable logic device (PLD), a controller microcontroller units, reduced instruction set computers (RISC), microprocessors, or the like, or any combination thereof. In some embodiments, the processing device 140 may be part of the medical device 110 or the terminal device 130. For example, the processing device 140 may be integrated into the medical device 110 for determining the target position of the scanned object in the scanning region, the abnormal points in the scanned image, and the recommended scanning protocol, etc.

The storage device 150 may store data, an instruction, and/or any other information. For example, the storage device 150 may store the scanned image obtained by the medical device 110 and information related thereto, etc. In some embodiments, the storage device 150 may store data obtained from the medical device 110, the at least one terminal device 130, and/or the processing device 140. In some embodiments, the storage device 150 may store data and/or instructions that the processing device 140 may perform or use to perform exemplary methods described in this present disclosure. In some embodiments, the storage device 150 may include a mass storage, a removable memory, a volatile read-and-write memory, a read-only memory (ROM), or the like, or any combination thereof. In some embodiments, the storage device 150 may be implemented on a cloud platform.

In some embodiments, the storage device 150 may be connected to the network 120 to communicate with at least one other component (e.g., the medical device 110, the at least one terminal device 130, the processing device 140) of the system 100. The at least one component of the system 100 may access data stored in the storage device 150 (e.g., a scanned image of the scanned object, information data, etc.) via the network 120. In some embodiments, the storage device 150 may be part of the processing device 140.

It should be noted that the above description is merely provided for the purposes of illustration, and not intended to limit the scope of the present disclosure. For persons having ordinary skills in the art, multiple variations and modifications may be made under the teachings of the present disclosure. The features, structures, methods, and other characteristics of the exemplary embodiments described in the present disclosure may be combined in various ways to obtain additional and/or alternative exemplary embodiments. For example, the storage device 150 may be a data storage device that includes a cloud computing platform (e.g., a public cloud, a private cloud, a community cloud, and a hybrid cloud, etc.). However, those variations and modifications do not depart from the scope of the present disclosure.

Figure 2:
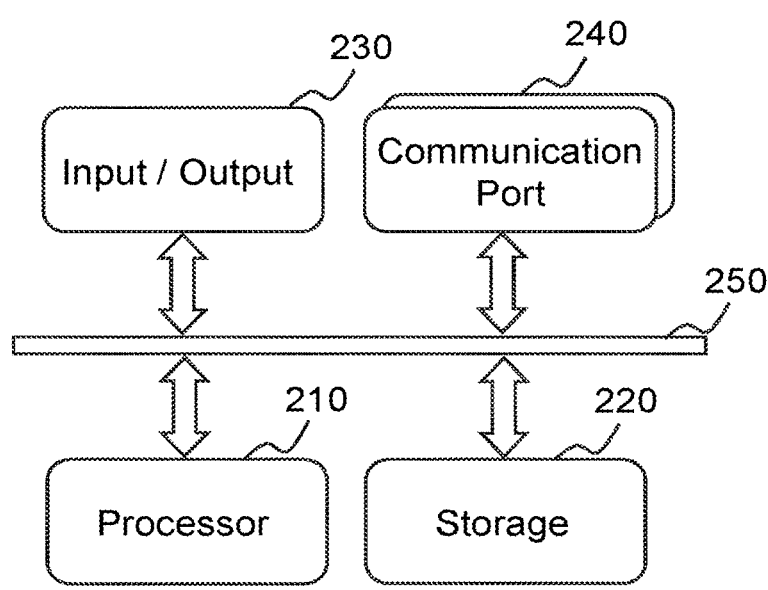
FIG. 2 is a schematic diagram illustrating hardware and/or software of an exemplary computing device according to some embodiments of the present disclosure.

FIG. 2 is a schematic diagram illustrating hardware and/or software of an exemplary computing device according to some embodiments of the present disclosure.

As shown in FIG. 2, in some embodiments, the computing device 200 may include a processor 210, a storage 220, an input/output interface 230, a communication port 240, and a bus 250.

The processor 210 may perform computer instructions (e.g., program codes) and perform functions of the image scanning system 100 of the medical device described in the present disclosure. The computer instructions may include programs, objects, components, data structures, procedures, modules, and functions, which perform particular functions described herein. For example, the processor 210 may process a scanned image obtained from any component of the system 100. In some embodiments, the processor 210 may include a microcontroller, a microprocessor, a reduced instruction set computer (RISC), an application-specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or a combination thereof. Merely for illustration, only one processor is described in the computing device 200. However, it should be noted that the computing device 200 in the present disclosure may also include multiple processors.

The storage 220 may store data/information obtained from any other component of the system 100. In some embodiments, the storage 220 may include a mass storage, a removable storage, a volatile read-and-write memory, a read-only memory (ROM), or the like, or a combination thereof. Exemplary mass storage may include a disk, an optical disk, a solid state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), a digital versatile disk ROM, etc.

The input/output interface 230 may be configured to input or output signals, data, or information. In some embodiments, the input/output interface 230 may enable a user interaction with components of the system 100 (e.g., the medical device 110). In some embodiments, the input/output interface 230 may include an input device and an output device. Exemplary input device may include a keyboard, a mouse, a touch screen, a microphone, or the like, or any combinations thereof. Exemplary output device may include a display device, a speaker, a printer, a projector, or the like, or any combination thereof. Exemplary display device may include a liquid crystal display (LCD), a light emitting diode (LED) based display, a flat panel display, a curved display, a television device, a cathode ray tube (CRT), or the like, or any combinations thereof.

The communication port 240 may be connected to a network to facilitate data communications. The connection may be a wired connection, a wireless connection, or a combination thereof. The wired connection may include a cable, a fiber optic cable, a telephone wire, or the like, or any combinations thereof. The wireless connection may include a Bluetooth link, a Wi-Fi link, a WiMax link, a WLAN link, a ZigBee link, a mobile network link (e.g., 3G, 4G, 5G, etc.), or the like, or any combinations thereof. In some embodiments, the communication port 240 may be a standardized communication port, such as RS232, RS485, etc. In some embodiments, the communication port 240 may be a specially designed communication port. For example, the communication port 240 may be designed in accordance with the digital imaging and communications in medicine (DICOM) protocol.

The bus 250 may include hardware and/or software for coupling the components of the computing device 200 to each other. In some embodiments, the bus 250 may include a data bus, an address bus, a control bus, an expansion bus, and a local bus. In some embodiments, the bus 250 may include an accelerated graphics port (AGP) or other graphics bus, an extended industry standard architecture (EISA) bus, a front side bus (FSB), a hyper transport (HT) interconnect, an industry standard architecture (ISA) bus, an InfiniBand interconnect, a low pin count (LPC) bus, a memory bus, a micro channel architecture (MCA) bus, a peripheral component interconnect (PCI) bus, a PCI-Express (PCI-X) bus, a serial advanced technology attachment (SATA) bus, a video electronics standards association local bus (VLB), or their VLB), or the like, or any combinations thereof. In some embodiments, the bus 250 may include one or more buses. Although specific buses are described and illustrated in the embodiments of the present disclosure, the present disclosure includes any suitable bus or interconnect.

Figure 3:
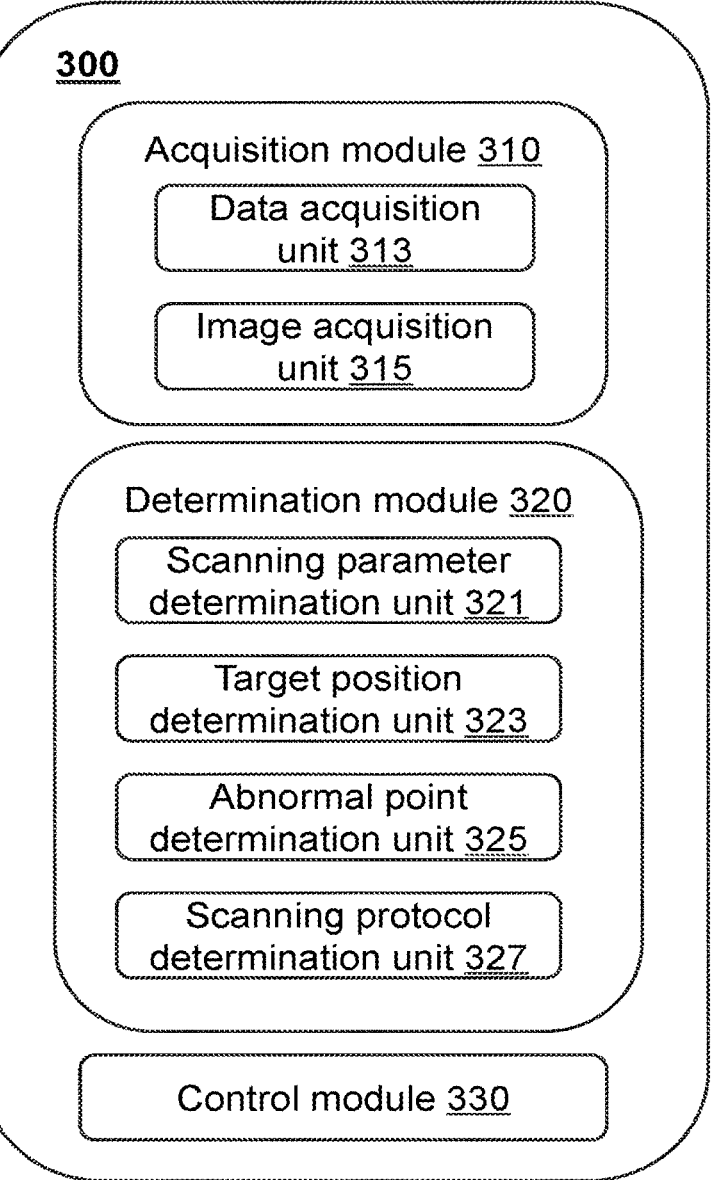
FIG. 3 is a block diagram illustrating an exemplary image scanning system according to some embodiments of the present disclosure.

FIG. 3 is a block diagram illustrating an exemplary image scanning system according to some embodiments of the present disclosure.

As shown in FIG. 3, in some embodiments, the image scanning system 300 may include an acquisition module 310, a determination module 320, and a control module 330.

The acquisition module 310 may be configured to obtain data. For example, the acquisition module 310 may be configured to obtain information data, positional information, a positioning image, scanning data, a scanned image of the scanned object, input information of a user, or the like, or any combination thereof.

In some embodiments, the acquisition module 310 may include a data acquisition unit 313 and an image acquisition unit 315. The data acquisition unit 313 may be configured to obtain the information data, the positional information, the scanning data of the scanned object, the input information of the user, or the like, or any combination thereof. The image acquisition unit 315 may be configured to obtain the positioning image and/or the scanned image of the scanned object, etc.

The determination module 320 may be configured to determine a target position of the scanned object in a scanning region of a medical device. In some embodiments, the determination module 320 may be configured to determine at least one abnormal point in the scanned image. For example, the determination module 320 may be configured to determine at least one abnormal point in a tomographic image. As another example, the determination module 320 may be configured to determine at least one corresponding abnormal point in different scanned images. In the present disclosure, the corresponding abnormal points in the different scanned images refer to that the abnormal points in the different scanned images correspond the same (approximately) part of the same scanned object presented in the scanned images. In the present disclosure, the "approximately" means that a deviation from the situation (e.g., the same part) described is less than a threshold value. For example, the corresponding abnormal points in the different scanned images refer to that a proportion of the abnormal points corresponding to the same part of the same scanned object is higher than 80%, 90%, 95%, or the like.

In some embodiments, the determination module 320 may include a scanning parameter determination unit 321, a target position determination unit 323, an abnormal point determination unit 325, and a scanning protocol determination unit 327. The scanning parameter determination unit 321 may be configured to determine scanning parameters. For example, the scanning parameter determination unit 321 may determine at least one scanning parameter based on the information data, the positional information, and/or the positioning image of the scanned object. The target position determination unit 323 may be configured to determine a target position of the scanned object in a scanning region. For example, the target position determination unit 323 may determine the target position of the scanned object in the scanning region of the medical device based on the scanning parameters, the positional information, and/or parameters (e.g., partitions of the scanning region of the medical device, a sensitivity of each partition, etc.) of the medical device. The abnormal point determination unit 325 may be configured to determine abnormal points in the scanned image. For example, the abnormal point determination unit 325 may be configured to determine at least one glucose metabolism abnormal point in a first PET scanning image. As another example, the abnormal point determination unit 325 may be configured to determine at least one second abnormal point in a tomographic image, and/or at least one third abnormal point in a second scanned image. The scanning protocol determination unit 327 may be configured to determine a recommended scanning protocol. In some embodiments, the scanning protocol determination unit 327 may be configured to recommend a scanning protocol to the user.

The control module 330 may be configured to control the medical device. For example, the control module 330 may control the scanning couch to move the scanned object to the target position. As another example, the control module 330 may control the medical device to perform a scanning on the scanned object.

It should be noted that the above description of the image scanning system 300 and its modules is merely provided for the purposes of illustration, and not intended to limit the scope of the present disclosure. It can be understood that it is possible for persons having ordinary skills in the art, with an understanding of the principle of the system, to make any combination of individual modules or to form subsystems to connect to other modules without departing from the principle. For example, in some embodiments, the acquisition module 310, the determination module 320, and the control module 330 in FIG. 3 may be different modules in a single device (e.g., the processing device 140), or a single module that implements two or more of the above functions. As another example, each module may have a storage module. As a further example, the modules may share a storage module. Those variations and modifications do not depart from the scope of the present disclosure.

FIG. 4 is a flow chart illustrating an exemplary image scanning method according to some embodiments of the present disclosure.

In some embodiments, the image scanning method 400 may be performed by the image scanning system 100 or the image scanning system 300. For example, the image scanning method 400 may be stored in a storage device (e.g., the storage device 150) in a form of programs or instructions, when executing the programs or instructions, the image scanning system 100 (e.g., the processing device 140) may implement the image scanning method 400. The operations of the image scanning method 400 presented below are intended to be illustrative. In some embodiments, the image scanning method 400 may be accomplished with one or more additional operations not described and/or without one or more of the operations discussed. Additionally, the order of the operations of the image scanning method 400 illustrated in FIG. 4 and described below is not intended to be limiting.

In 402, a target position of a scanned object in a scanning region of the medical device may be determined. In some embodiments, operation 402 may be performed by the medical device 110, the processing device 140, or the determination module 320 (e.g., the target position determination unit 323).

The target position may reflect a corresponding relationship between a target scanning site of the scanned object and a scanning region of the medical device. In some embodiments, in response to that the scanned object is located at the target position, the target scanning site of the scanned object may be located in the scanning region of the medical device. For example, since a scanning region of a short-axis PET scanning system with an axial length less than or equal to 0.3 m cannot completely cover the scanned object, a scanning couch may be gradually moved multiple times to place the target scanning site of the scanned object into the scanning region of the PET scanning system to obtain the scanned image of the target scanning site. In some embodiments, a geometric center of the target scanning site may (roughly) coincide with a center of the scanning region of the medical device when the scanned object is located at the target position, i.e., a deviation between the geometric center of the target scanning site and the center of the scanning region of the medical device is less than a threshold value (e.g., 10%, 5%, etc., or 5 mm, 3 mm, 1 mm, etc.).

In some embodiments, in response to that the scanned object is located at the target position, the target scanning site of the scanned object may be located in a high-sensitivity scanning region of the medical device. A sensitivity of the medical device refers to its detection efficacy. In the case of a PET scanner, the sensitivity may refer to the detection efficacy of the PET scanner for annihilation events, and the higher sensitivity, the more signals are detected for the same activity of the radioactive source, and accordingly the higher the image quality. For example, due to a sensitivity curve of a long-axis PET scanning system with an axial length greater than or equal to 0.75 m, different positions of a scanning region may correspond to different sensitivities, and accordingly different scanning positional manners have different scanning effects. In some embodiments, the scanning region may be divided into a plurality of sub-regions based on a sensitivity distribution and/or geometric structure parameters of the scanning region of the medical device. A sub-region with a sensitivity higher than a preset threshold may be defined as a high-sensitivity scanning region. More descriptions regarding the division of the scanning region may be found elsewhere in the present disclosure (e.g., FIG. 6 and the description thereof).

In some embodiments, a scanning range of the scanned object may be determined. A geometric center of the scanning range may be determined. According to the geometric center and the center of the scanning region of the medical device, a target position may be determined. For example, the processing device 140 may obtain the scanning range of the scanned object that is input by a medical staff I through the selection of a scanning box in a display interface of the terminal device 130, and determine the geometric center of the scanning range. Further, the processing device 140 may determine a position where the geometric center coincides with the center of the scanning region as the target position.

In some embodiments, scanning parameters may be determined. The target position of the scanned object in the scanning region of the medical device may be determined based on the scanning parameters. In some embodiments, the scanning parameters may include a scanning range of the scanned object, position points within the scanning range, and/or a scanning duration. The position points in the scanning range may be a center point of the scanned object in the scanning range. In some embodiments, the position points in the scanning range may be determined based on a body shape, a geometric structure, etc. of the scanned object. The scanning duration may be a detection duration for the medical device to scan the scanned object, for example, 20 minutes, 30 minutes, etc. In some embodiments, the scanning parameters may be determined based on the information data and/or the positioning image of the scanned object. More descriptions regarding the determination of the scanning parameters based on the information data and/or the positioning image may be found elsewhere in the present disclosure (e.g., FIGS. 5-8 and the description thereof).

In 404, the scanned object may be moved to the target position. In some embodiments, operation 404 may be performed by the medical device 110, the processing device 140, or the control module 330.

In some embodiments, the scanned object may be moved to the target position by controlling the scanning couch. For example, a control signal may be sent via the processing device 140 to a driver of the scanning couch 112. The driver of the scanning couch 112 may drive, for example, a chassis drive wheel based on the control signal, thereby moving the scanned object to the target position. In some embodiments, whether to move the scanned object to the target position may be determined based on a position relationship between the scanning couch and the scanner. In some embodiments, an image containing the scanned object and the scanner may be obtained, and whether to move the scanned object to the target position may be determined based on the position relationship between the scanned object and the scanner in the image. In some embodiments, whether to move the scanned object to the target position may be determined in any other feasible manner, which is not limited by the present disclosure.

In 406, the medical device may be controlled to perform a scanning on the scanned object to obtain a scanned image of the scanned object. In some embodiments, operation 406 may be performed by the medical device 110, the processing device 140, or the control module 330.

In some embodiments, when it is determined that the scanned object is located at the target position, the medical device may be controlled to perform the scanning on the scanned object. For example, a PET scanner may be controlled to perform a PET scanning on the scanned object and obtain a corresponding PET scanned image.

In 408, at least one abnormal point in the scanned image may be determined. In some embodiments, operation 408 may be performed by the medical device 110, the processing device 140, or the determination module 320 (e.g., the abnormal point determination unit 325).

In some embodiments, the at least one abnormal point in the scanned image may be determined based on the scanned image obtained in operation 406. In some embodiments, the at least one abnormal point in the scanned image may be determined based on a machine learning model. For example, the processing device 140 may identify and mark the at least one abnormal point in the scanned image based on the machine learning model.

In some embodiments, the scanned image obtained in operation 406 may be a first PET scanned image obtained by performing, by a PET scanner, a scanning on the scanned object. In some embodiments, the at least one abnormal point in the first PET scanned image may include at least one glucose metabolism abnormal point. The abnormal glucose metabolism indicates an abnormal standard uptake value (SUV) of the scanned object. The SUV may be used for the identification of benign and malignant tumors and the evaluation of curative effects, etc. The abnormal SUV value indicates a presence of a lesion such as a malignant tumor.

In 410, a scanning protocol may be recommended based on the at least one abnormal point. In some embodiments, operation 410 may be performed by the medical device 110, the processing device 140, or the determination module 320 (e.g., the scanning protocol determination unit 327).

The scanning protocol may refer to a scanning parameter or a scanning parameter group used by the medical device to perform a scanning. In some embodiments, the existence of the abnormal point in the scanned image may indicate that the scanned object may have a lesion such as a malignant tumor. In such cases, it is necessary to further scan and analyze the scanned object to determine whether the scanned object has a lesion such as a malignant tumor. In some embodiments, if the at least one abnormal point is identified in the scanned image, a corresponding scanning protocol may be recommended based on the abnormal point. For example, if the abnormal point is the glucose metabolism abnormal point, a delayed scanning protocol corresponding to the glucose metabolism abnormal point may be recommended. More descriptions regarding the recommending of the scanning protocol may be found elsewhere in the present disclosure (e.g., FIG. 16 and the description thereof).

In 412, the medical device may be controlled to perform a scanning on the scanned object based on the scanning protocol. In some embodiments, operation 412 may be performed by the medical device 110, the processing device 140, or the control module 330.

In some embodiments, the recommended scanning protocol may be displayed on an interactive interface of the medical device or a terminal device (e.g., the terminal device 130) to prompt a user (e.g., a medical staff) to confirm the recommended scanning protocol. In some embodiments, the recommended scanning protocol may be displayed at a position of the abnormal point in the scanned image. In some embodiments, the recommended scanning protocol may be displayed in any reasonably practicable manner, e.g., a pop-up display, a voice prompt, or a magnifying display light, which is not limited in the present disclosure. In some embodiments, if there is a deviation or shortage in the recommended scanning protocol, the user may manually modify the recommended scanning protocol. In some embodiments, the scanning may be performed on the scanned object according to the scanning protocol confirmed by the user. In some embodiments, the scanning in operation 412 may include a PET scanning and/or a CT scanning, etc.

In some embodiments, the scanning in operation 406 and operation 412 may be different modal scanning. For example, the medical device may include a first modal imaging device and a second modal imaging device. The scanning in operation 406 may be performed by the first modal imaging device. The scanning in operation 412 may be performed by the second modal imaging device. In some embodiments, the first modal imaging device may include a PET scanner, and the second modal imaging device may include a CT scanner. More descriptions regarding multi-modal scanning may be found elsewhere in the present disclosure (e.g., FIG. 16 and the description thereof).

In some embodiments, the target position of the scanned object in the scanning region of the medical device may be determined based on the confirmed scanning protocol, and the scanned object may be moved to that target position to be performed a further scanning. In some embodiments, the target position of the scanned object in the scanning region of the medical device may be determined based on at least one abnormal point in the scanned image, and the scanned object may be moved to the target position to be performed a further scanning.

It should be noted that the operations illustrated in the method 400 or the flowchart in FIG. 4 may be performed by a computer system including a set of computer-executable instructions. In addition, although the order of the operations of the method 400 or the flowchart in FIG. 4 is illustrated, in some cases, the operations may be performed in an order different from that shown herein.

A PET scanning system may include a short-axis PET scanner and a long-axis PET scanner. For the short-axis PET scanner, a PET scanning requires a medical staff to manually drag a scanning box on an interactive interface to plan a scanning range of the scanned object, and the PET scanning is performed by gradually moving the scanning couch multiple times. The long-axis PET scanner has a scanning aperture with a longer axial length (e.g., greater than or equal to 0.75 m), which allows simultaneous scanning or imaging of multiple parts of the scanned object or a larger region inside the scanning aperture.

Due to a sensitivity curve of the long-axis PET scanner, different scanning positional manners have different scanning effects. In some embodiments, the scanning position of the scanned object may be planned by manually dragging, by the medical staff, the scanning box in the interactive interface of the long-axis PET scanner, in which neither the sensitivity distribution curve of the PET scanner nor the different imaging requirements of different diseases are considered, so that the obtained scanned images are less targeted.

Embodiments of the present disclosure provide an image scanning method. The method may include obtaining information data of a scanned object in a medical system. The method may include determining at least one scanning parameter based on the information data, and then determining a target position of the scanned object in a scanning region of a medical device (e.g., a PET scanner) based on the scanning parameter. The method may include controlling a scanning couch to move the scanned object to the target position to scan the scanned object. The determination of the target position in the method takes into account that different scanned objects require different target positions, which avoids the planning of the scanning range by the medical staff by dragging the scanning box, accordingly enables the determination of the scanning range more accurate, so that the collected data is more accurate and generated images is clearer.

Figure 5:
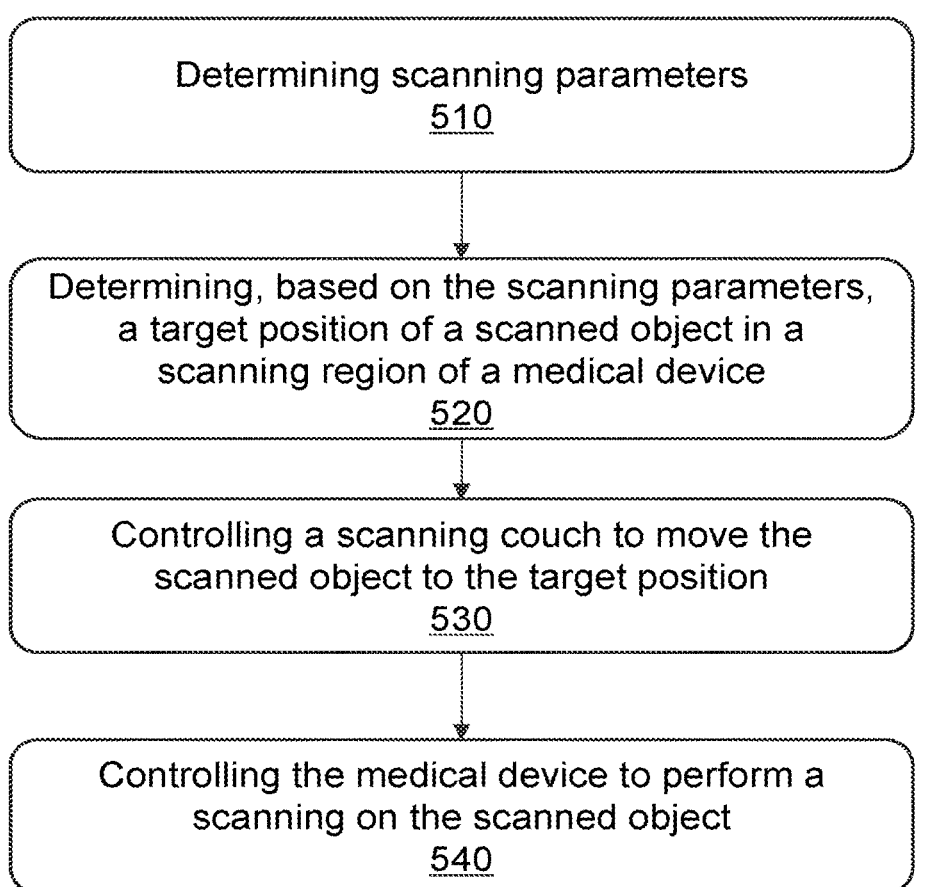
FIG. 5 is a flowchart illustrating an exemplary image scanning method according to some embodiments of the present disclosure.

FIG. 5 is a flowchart illustrating an exemplary image scanning method according to some embodiments of the present disclosure.

In some embodiments, the image scanning method 500 may be performed by the image scanning system 100, the image scanning system 300, or an image scanning device 1500. For example, the image scanning method 500 may be stored in a storage device (e.g., the storage device 150) in a form of programs or instructions, when executing the programs or instructions, the image scanning system 100 (e.g., the processing device 140) may implement the image scanning method 500. The operations of the image scanning method 500 presented below are intended to be illustrative. In some embodiments, the image scanning method 500 may be accomplished with one or more additional operations not described and/or without one or more of the operations discussed. Additionally, the order of the operations of the image scanning method 500 illustrated in FIG. 5 and described below is not intended to be limiting.

In 510, scanning parameters may be determined. In some embodiments, operation 510 may be performed by the processing device 140, the medical device 110, the determination module 320 (e.g., the scanning parameter determination unit 321), or a scanning parameter determination module 1520.

In some embodiments, the scanning parameters may include a scanning range of the scanned object, position points within the scanning range, and/or a scanning duration, etc. In some embodiments, the scanning parameters may be determined based on at least one of information data and positioning image of the scanned object. More descriptions regarding the determination of the scanning parameters may be found elsewhere in the present disclosure (e.g., FIGS. 6-8 and the description thereof).

In 520, a target position of a scanned object in a scanning region of the medical device may be determined based on the scanning parameters. In some embodiments, operation 520 may be performed by the processing device 140, the medical device 110, the determination module 320 (e.g., the target position determination unit 323), or a target position determination module 1530.

The target position may reflect a corresponding relationship between a target scanning site of the scanned object and a scanning region of the medical device. In some embodiments, in response to that the scanned object is located at the target position, the target scanning site of the scanned object may be located in a high-sensitivity scanning region of the medical device. In some embodiments, the target position of the scanned object in the medical device may be determined based on the positional information and the scanning parameters. In some embodiments, the scanning region may be divided into a plurality of sub-regions based on a sensitivity distribution and/or geometrical structure parameters of the scanning region of the medical device. Further, the target position of the scanned object in the scanning region may be determined based on the scanning parameters and an extent of the sub-regions. More descriptions regarding the determination of the target position may be found elsewhere in the present disclosure (e.g., FIGS. 6-8 and the description thereof).

In 530, a scanning couch may be controlled to move the scanned object to the target position. In some embodiments, operation 530 may be performed by the processing device 140, the medical device 110, the control module 330, or a control module 1540.

In some embodiments, a control signal may be sent to the scanning couch to instruct the scanning couch to move the scanned object to the target position. For example, the processing device 140 may send the control signal to a driver of the scanning couch 112. The driver of the scanning couch 112 may drive, for example, a chassis drive wheel based on the control signal to move the scanned object to the target position.

In 540, the medical device may be controlled to perform a scanning on the scanned object. In some embodiments, operation 540 may be performed by the processing device 140, the medical device 110, the control module 330, or a scanning module 1550.

The medical device (e.g., a PET scanner) may be controlled to perform the scanning on the scanned object after the scanned object has been moved to the target position.

FIG. 6 is a flowchart illustrating an exemplary image scanning method according to some embodiments of the present disclosure.

In some embodiments, the image scanning method 600 may be performed by the image scanning system 100, the image scanning system 300, or the image scanning device 1500. For example, the image scanning method 600 may be stored in a storage device (e.g., the storage device 150) in a form of programs or instructions, when executing the programs or instructions, the image scanning system 100 (e.g., the processing device 140) may implement the image scanning method 600. The operations of the image scanning method 600 presented below are intended to be illustrative. In some embodiments, the image scanning method 600 may be accomplished with one or more additional operations not described and/or without one or more of the operations discussed. Additionally, the order of the operations of the image scanning method 600 illustrated in FIG. 6 and described below is not intended to be limiting.

As shown in FIG. 6, in some embodiments, information data of a scanned object may be obtained. Scanning parameters may be determined based on the information data.

In 613, the information data of the scanned object may be obtained. In some embodiments, operation 612 may be performed by the medical device 110, the processing device 140, the acquisition module 310 (e.g., the data acquisition unit 313), or the data acquisition module 1510.

In some embodiments, the information data of the scanned subject may be obtained from a medical information system. In some embodiments, the information data of the scanned object may include identity information and medical information of the scanned object, or the like. The identity information may include information such as age, name, address, contact information, gender, etc. of the scanned object. The medical information may include information such as height, weight, stature, disease type, lesion information, etc. of the scanned subject.

In some embodiments, after a scanned object enters a hospital, a file would be established in a medical information system first, that is, the information data of the scanned object would be stored in the medical information system. In some embodiments, the medical information system may include, but is not limited to, a hospital information system (HIS), a laboratory information management system (LIS), a medical image archiving and communication system (PACS), and a radiology information system (RIS), etc. The hospital information system refers to an information system that provides comprehensive automatic management and various services for the overall operation of the hospital by using modern means such as computer hardware and software technology and network communication technology to comprehensively manage the flow of people, logistics and financial flow of the hospital and its various departments, and to collect, store, process, extract, transmit, aggregate data generated in various stages of medical activities to form various information. The radiology information system is a computer information system that performs process management based on the tasks of hospital imaging department workflow, which mainly realizes the computer network control and management of medical imaging inspection workflow, and the sharing of medical graphic information, so as to realize telemedicine. In some embodiments, the medical information system may include information that the scanned object retains at the current hospital and/or other hospitals. In some embodiments, a processing device may obtain the information data of the scanned object from the storage device 150 or other data sources (e.g., an external storage device independent of the system 100).

In 614, scanning parameters may be determined based on the information data of the scanned object. In some embodiments, operation 614 may be performed by the medical device 110, the processing device 140, the determination module 320 (e.g., the scanning parameter determination unit 321), or the scanning parameter determination module 1520.

The scanning parameters may refer to parameter data used by a medical device when the scanned object is scanned by the medical device. In some embodiments, at least one scanning parameter may be determined based on the obtained information data of the scanned object including the identity information and the medical information. In some embodiments, the scanning parameters may include a scanning range of the scanned object, position points within the scanning range, and/or a scanning duration, etc. The scanning range corresponds to a scanning part of interest of the scanned object, e.g., head, torso, etc. The position points within the scanning range are reference points corresponding to the scanning part of interest of the scanned object, e.g., a center point of the head or the torso. In some embodiments, the position points within the scanning range may be determined based on a body shape and/or geometry of the scanned object. The scanning duration corresponds to a length of time that the medical device scans the scanned object, e.g., 15 minutes, 20 minutes, 50 minutes, etc.

In some embodiments, the at least one scanning parameter may be determined by a machine learning model such as a deep learning model. In some embodiments, information data of patients in various hospitals may be obtained in advance. A training set may be established based on the information data of the patients, and a trained deep learning model may be obtained by training an initial neural network model based on the training set. The information data of each patient may include identity information and medical information of the patient, a scanning range, position points in the scanning range, or a scanning duration corresponding to the patient, etc. In the embodiments, the processing device may input the obtained information data of the scanned object into the trained deep learning model to obtain the scanning parameters, i.e., at least one of the scanning range, the position points within the scanning range, or the scanning duration, etc., associated with the scanned object.

In some embodiments, the scanning parameters may be determined based on an input by a user. For example, the processing device 140 may display the information data of the scanned object on an interactive interface of the medical device 110 or terminal device 130, and a medical staff may manually type in or select the scanning parameters based on the information data of the scanned object displayed on the interactive interface. In some embodiments, the scanning parameters may be recommended to the user based on the information data of the scanned object, and the scanning parameters may be determined based on the selection of the user. In some embodiments, the scanning parameters manually input by the user may be obtained. For example, the processing device 140 may obtain the scanning parameters such as a scanning range, position points within the scanning range, and/or a scanning duration manually input by a patient or the medical staff through the interactive interface of the medical device 110 or terminal device 130. In some embodiments, the scanning parameters may be determined by any other feasible means, which is not limited in the present disclosure.

In 620, a target position of the scanned object in scanning region of the medical device may be determined based on the scanning parameters. In some embodiments, operation 620 may be performed by the medical device 110, the processing device 140, the determination module 320 (e.g., the target position determination unit 323), or the target position determination module 1530.

In some embodiments, the target position of the scanned object in the medical device may be determined based on the scanning parameters, positional information of the scanned object, and/or a sensitivity distribution of the scanning region of the medical device. The positional information corresponds to a posture of the scanned object on the scanning couch. Merely by way of example, the positional information may include that the scanned object lies sideways on the scanning couch, that the scanned object lies flat on the scanning couch, that the scanned object is curled up (e.g., the scanned object's legs cannot be stretched) on the scanning couch, etc. In some embodiments, the positional information may include an orientation of the scanned object on the scanning couch. For example, if a direction in which the scanning couch enters the medical device is defined as an entrance direction, and a direction in which the scanning couch comes out from the medical device as an exit direction, the positional information may include that the scanning object's head faces the entrance direction of the scanning couch or the scanning object's feet faces the inlet direction of the scanning couch, etc.

In some embodiments, the positional information of the scanned object may be obtained from the medical device (e.g., the medical device 110). In some embodiments, the processing device may obtain the positional information of the scanned object from a terminal device (e.g., the terminal device 130). For example, the medical staff may input the positional information of the scanned object into the image scanning system 100 in real time via the interactive interface of the medical device 110 or the terminal device 130 based on the posture of the scanned object on the scanning couch. Specifically, when the scanning parameters are determined, a positional information list containing various positional information may be displayed in the interactive interface of the medical device (e.g., a PET scanner). The target position of the scanned object in the scanning region of the medical device may be determined based on the positional information list and the input of the user. The input refers to positional information of the scanned object input by the user (e.g., a medical staff) based on the positional information list. In some embodiments, the input may be information input by the user via a mouse or keyboard, or information automatically generated by the system via an external sensor signal. For example, when the scanning parameters are head scanning, the medical staff may select positional information corresponding to the scanned object from the positional information list, and the processing device 140 may determine the target position of the scanned object in the scanning region of the PET scanner based on the positional information and the scanning parameters.

In some embodiments, the positional information may be displayed in the interactive interface of the medical device in a form of a medical icon, a geometric figure, or a text list. The user may select corresponding positional information based on an actual condition of the scanned object. The medical icon may display the positional information in a form of an icon with medical information. The geometric figure may display the positional information in a form of a graph such as a rectangle, triangle, etc. The text list may display the positional information in a form of a text description.

In some embodiments, the positional information of the scanned object may be determined based on a photographic image including the scanned object. For example, the processing device may obtain the photographic image containing the scanned object via a camera device, determine the positional information of the scanned object by image identification, and/or store the positional information in the medical device. In some embodiments, a scanning protocol and/or scanning parameters may be automatically recommended based on the positional information. The recommended scanning protocol and/or scanning parameters may be displayed in the interactive interface of the medical device. In some embodiments, the processing device may determine the positional information based on a positioning image of the scanned object. For example, the processing device may determine the positional information of the scanned object based on a tomographic image of the scanned object.

In the prior art, a center of the scanning region of the medical device (e.g., the PET scanner) is defaulted as the target position. Unlike the prior art, in the embodiments of the present disclosure, the target position of the scanned object in the scanning region of the medical device may be determined based on the scanning parameters and the positional information, which enables a target scanned part of the scanned object to be placed in a high-sensitivity region of the scanning region based on parameters of the medical device itself, thereby increasing a count rate of a region of interest detected by the medical device and improving the image quality of the scanned image.

In some embodiments, the scanning region of the medical device, such as a PET scanner, may be divided into a plurality of sub-regions based on a sensitivity distribution of the scanning region of the medical device. The target position may be set in a sub-region with a sensitivity higher than a preset threshold. In the case of a PET scanner, the sensitivity may refer to the detection efficacy of the PET scanner for annihilation events, and the higher sensitivity, the more signals are detected for the same activity of the radioactive source, and accordingly the higher the image quality. The sensitivities of the plurality of sub-regions are different, and the sub-region with a sensitivity higher than the preset threshold is a high-sensitivity region. The target position is set in the high-sensitivity region, which may improve the image quality of the scanned image obtained by the medical device. In some embodiments, the preset threshold may be determined based on the number of sub-regions to be divided. For example, if the scanning region is divided, based on the sensitivity, into six sub-regions including a first sub-region, a second sub-region, a third sub-region, a fourth sub-region, a fifth sub-region, and a sixth sub-region arranged in sequence along an axial direction of a scanning chamber of the medical device. The third sub-region and the fourth sub-region have a highest sensitivity and are the same or close to the same sensitivity. The second sub-region and the fifth sub-region have a medium sensitivity. The first sub-region and the sixth sub-region have a low sensitivity. Merely by way of example, the sensitivities of the third sub-region and the fourth sub-region may be defined as 2; the sensitivities of the first sub-region and the sixth sub-region may be defined as 0, and the sensitivities of the second sub-region and the fifth sub-region may be defined as 1, accordingly, the preset threshold may be set as 1, and the sub-regions with a sensitivity greater than 1 may be high sensitivity regions. In some embodiments, the sensitivity corresponding to each sub-region and the preset threshold may be adjusted. For example, if the scanning region is divided, based on the sensitivity, into seven sub-regions including a first sub-region, a second sub-region, a third sub-region, a fourth sub-region, a fifth sub-region, a sixth sub-region, and a seventh sub-region arranged in sequence along the axial direction of the scanning chamber of the medical device. The sensitivity of the fourth sub-region may be defined as 4; the sensitivities of the third sub-region and fifth sub-region may be defined as 3; the sensitivities of the second sub-region and the sixth sub-region may be defined as 2; and the sensitivities of the first sub-region and the seventh sub-region may be defined as 1, accordingly, the preset threshold may be set as 2, and the sub-regions with a sensitivity greater than 2 and less than or equal to 3 or 4 may be high sensitivity regions. In some embodiments, the processing device may determine the target position of the scanned object in the scanning region of the medical device (e.g., the PET scanner) based on the scanning parameters (and/or the positional information) of the scanned object and an extent of the sub-regions of the medical device.

In some embodiments, the scanning region of the medical device (e.g., the PET scanner) may be divided into a plurality of sub-regions based on geometrical structural parameters of the medical device. In some embodiments, the geometrical structural parameters of the medical device (e.g., the PET scanner) may include a length of the scanning chamber or the number of detector detection units. Merely by way of example, FIG. 9 is a schematic diagram illustrating exemplary scanning sub-regions according to some embodiments of the present disclosure. As shown in FIG. 9, in some embodiments, the scanning region may be divided, based on the length of the scanning chamber of the medical device, into eight sub-regions including a first sub-region, a second sub-region, a third sub-region, a fourth sub-region, a fifth sub-region, a sixth sub-region, a seventh sub-region, and an eighth sub-region arranged in sequence along the axial direction of the scanning chamber of the medical device. The third sub-region, the fourth sub-region, the fifth sub-region, and the sixth sub-region are high-sensitivity regions, and the sensitivities of the four sub-regions are the same or close to the same. The second sub-region and the seventh sub-region are medium-sensitivity regions. The first sub-region and the eighth sub-region are low-sensitivity regions. In some embodiments, the widths of the eight sub-regions may be the same or different. For example, the widths of the eight sub-regions may be the same. In some embodiments, the processing device may determine positions, in the plurality of sub-regions, of various parts of the scanned object based on the scanning parameters and/or the positional information of the scanned object.

It should be understood that the above description regarding the number of the sub-regions is merely provided for the purposes of illustration. In some alternative embodiments, the scanning region may be divided into any reasonable number of sub-regions according to different conditions of the medical device, the scanned object, and a scanning environment. For example, the number of sub-regions may be two, three, five, ten, etc., which is not limited in the present disclosure.

Operations 630 and 640 are the same as operations 530 and 540 in the method 500, respectively, which are not repeated herein.

In the above image scanning method for the medical device, the target position of the scanned object in the scanning region of the medical device (e.g., the PET scanner) may be determined based on the scanning parameter that is determined based on the obtained information data of the scanned object, which not only avoids the planning of the scanning range by the medical staff by manually dragging a scanning box on the interactive interface, accordingly improves the scanning efficiency, but also takes into account that different scanned objects require different target positions, accordingly make the determination of the scanning range of the medical device more accurate, so that the collected data is more accurate and generated images is clearer.

FIG. 7 is a flowchart illustrating an exemplary image scanning method according to some embodiments of the present disclosure.

In some embodiments, the image scanning method 700 may be performed by the image scanning system 100, the image scanning system 300, or the image scanning device 1500. For example, the image scanning method 700 may be stored in a storage device (e.g., the storage device 150) in a form of programs or instructions, when executing the programs or instructions, the image scanning system 100 (e.g., the processing device 140) may implement the image scanning method 700. The operations of the image scanning method 700 presented below are intended to be illustrative. In some embodiments, the image scanning method 700 may be accomplished with one or more additional operations not described and/or without one or more of the operations discussed. Additionally, the order of the operations of the image scanning method 700 illustrated in FIG. 7 and described below is not intended to be limiting.

As shown in FIG. 7, in some embodiments, scanning parameters may be determined based on information data and a positioning image of a scanned object.

In 713, information data of the scanned object may be obtained. In some embodiments, operation 713 may be performed by the medical device 110, the processing device 140, the acquisition module 310 (e.g., the data acquisition unit 313), or the data acquisition module 1510.

In some embodiments, the information data of the scanned object may be obtained from a medical information system. In some embodiments, the information data of the scanned object may be obtained from the medical information system based on a number (e.g., a case number, an ID number, etc.) of the scanned object. Specifically, operation 713 is the same as operation 613, which is not repeated herein.

In 715, a positioning image of the scanned object may be obtained. In some embodiments, operation 715 may be performed by the medical device 110, the processing device 140, the acquisition module 310 (e.g., the image acquisition unit 315), or the data acquisition module 1510.

In some embodiments, the positioning image of the scanned subject may include one or more of a CT image of the scanned object, an MRI image of the scanned object, a natural image of the scanned object captured by a camera, or an echo image of the scanned object detected by radar. In some embodiments, the positioning image may reflect information such as a posture of the scanned subject in a scanning couch.

In 717, scanning parameters may be determined based on the information data and the positioning image. In some embodiments, operation 717 may be performed by the medical device 110, the processing device 140, the determination module 320 (e.g., the scanning parameter determination unit 321), or the scanning parameter determination module 1520.

In some embodiments, the scanning parameters may be determined by a trained deep learning model. For example, information data and positioning images of patients in various hospitals may be obtained in advance. A training set may be established based on the information data and positioning images, and a trained deep learning model may be obtained by training an initial neural network model based on the training set. In the embodiments, the obtained information data and positioning image of the scanned object may be input into the trained deep learning model to obtain the scanning parameters. In some embodiments, the scanning parameters may be determined based on an input by the user. For example, the processing device 140 may display the information data and the positioning image of the scanned object on an interactive interface of the medical device 110 or the terminal device 130, and a medical staff may manually type in or select the scanning parameters based on the information data and the positioning image of the scanned object displayed on the interactive interface. In some embodiments, the scanning parameters may be recommended to the user based on the information data and the positioning image, and the scanning parameters may be determined based on the selection of the user. In some embodiments, the scanning parameters may be determined by any other feasible means, which is not limited in the present disclosure.

Operations 720-740 correspond to operations 520-540 or operations 620-640, respectively, and more descriptions may be found in the relevant descriptions in FIG. 5 or FIG. 6, which is not repeated herein.

In the above-described image scanning method for a medical device, the target position of the scanned object in the scanning region of the medical device may be determined based on the scanning parameters that are determined based on the obtained information data and positioning image of the scanned object, which may simplify the process of setting up a scanning scheme and facilitate the user (e.g., a medical staff) to select different scanning schemes for different diseases, thereby optimizing the image quality.

FIG. 8 is a flowchart illustrating an exemplary image scanning method according to some embodiments of the present disclosure.

In some embodiments, the image scanning method 800 may be executed by the image scanning system 100, the image scanning system 300, or the image scanning device 1500. For example, the image scanning method 800 may be stored in a storage device (e.g., the storage device 150) in a form of programs or instructions, when executing the programs or instructions, the image scanning system 100 (e.g., the processing device 140) may implement the image scanning method 800. The operations of the image scanning method 800 presented below are intended to be illustrative. In some embodiments, the image scanning method 800 may be accomplished with one or more additional operations not described and/or without one or more of the operations discussed. Additionally, the order of the operations of the image scanning method 800 illustrated in FIG. 8 and described below is not intended to be limiting.

As shown in FIG. 8, in some embodiments, scanning parameters may be determined based on a positioning image of a scanned object.

In 815, the positioning image of the scanned object may be obtained. Specifically, operation 815 corresponds to operation 715, and more descriptions may be found in the relevant description in operation 715, which is not repeated herein.

In 819, the scanning parameters may be determined based on the positioning image. In some embodiments, operation 819 may be performed by the medical device 110, the processing device 140, the determination module 320 (e.g., the scanning parameter determination unit 321), or the scanning parameter determination module 1520.

In some embodiments, the scanning parameters may be determined by a trained deep learning model. For example, positioning images of patients in various hospitals, a corresponding scanning range, position points within the scanning range, and/or a scanning duration may be obtained in advance. A training set may be established based on the positioning image of the patients and corresponding scanning parameters, and a trained deep learning model may be obtained by training an initial neural network model based on the training set. In the embodiments, the obtained positioning image of the scanned object may be input into the trained deep learning model to obtain the scanning parameters.

In some embodiments, the scanning parameters may be determined based on an input by a user. For example, the processing device 140 may display the positioning image of the scanned object on an interactive interface of the medical device 110 or the terminal device 130, and a medical staff may manually type in or select the scanning parameters based on the positioning image of the scanned object displayed on the interactive interface. In some embodiments, the scanning parameters may be recommended to the user based on the positioning image, and the scanning parameters may be determined based on the selection of the user. In some embodiments, the scanning parameters may be determined by any other feasible means, which is not limited in the present disclosure.

In 820, a target position of the scanned object in a scanning region of the medical device may be determined based on the scanning parameters. In some embodiments, operation 820 may be performed by the medical device 110, the processing device 140, the determination module 320 (e.g., the target position determination unit 323), or the target position determination module 1530.

In some embodiments, positional information of the scanned object may be obtained. The scanning parameters of a scanning protocol in the medical device (e.g., a PET scanner) may be determined based on the positional information. The target position of the scanned object in the scanning region of the medical device (e.g., the PET scanner) may be determined based on the scanning parameters of the scanning protocol. For example, the positional information of the scanned object may be obtained, and the initial scanning parameters of the scanning protocol in the medical device (e.g., the PET scanner) may be updated based on the positional information. The target position of the scanned object in the scanning region of the medical device (e.g., the PET scanner) may be determined based on the updated scanning parameters of the scanning protocol. In some embodiments, the positional information of the scanned object may be determined based on the scanning parameters. For example, a mapping relationship between the scanning parameters and the positional information may be preset. According to the mapping relationship between the scanning parameters and the positional information, a positional position of the scanned object is automatically completed, and the positional information is updated to the scanning protocol. By automatically determining the positional information based on the scanning parameters and updating the scanning parameters of the scanning protocol in the medical device based on the positional information, the automation level of the medical device (e.g., the PET scanner) and the scanning efficiency may be improved.

Operations 820-840 are similar to operations 520-540, operations 620-640, or operations 720-740, respectively, and more descriptions may be found in the relevant descriptions in FIG. 5 or FIG. 6, which is not repeated herein.

In the above-described image scanning method for the medical device, the target position of the scanned object in the scanning region of the medical device (e.g., the PET scanner) may be determined based on the scanning parameters that are determined based on the obtained positioning image, which may simplify the process of setting up a scanning scheme and facilitate the user (e.g., a medical staff) to select different scanning schemes for different diseases, thereby optimizing the image quality.

In some embodiments, for example, due to a sensitivity curve of a long-axis PET scanner, different scanning positional manners (i.e., different target positions) have different scanning effects. In some embodiments, an axial length of the long-axis PET scanner is greater than or equal to 0.75 m. In some embodiments, the image scanning method provided in the embodiments may be configured to determine the scanning parameters of the PET scanner based on the information data and/or the positioning image of the scanned object, determine the target position of the scanned object in the scanning region of the PET scanner based on the scanning parameters and the positional information of the scanned object, and execute a PET scanning after the scanned object is moved to the target position to obtain a better quality scanned image.

FIGS. 10-14 are schematic diagrams illustrating exemplary positional manners according to some embodiments of the present disclosure.

Figure 10:
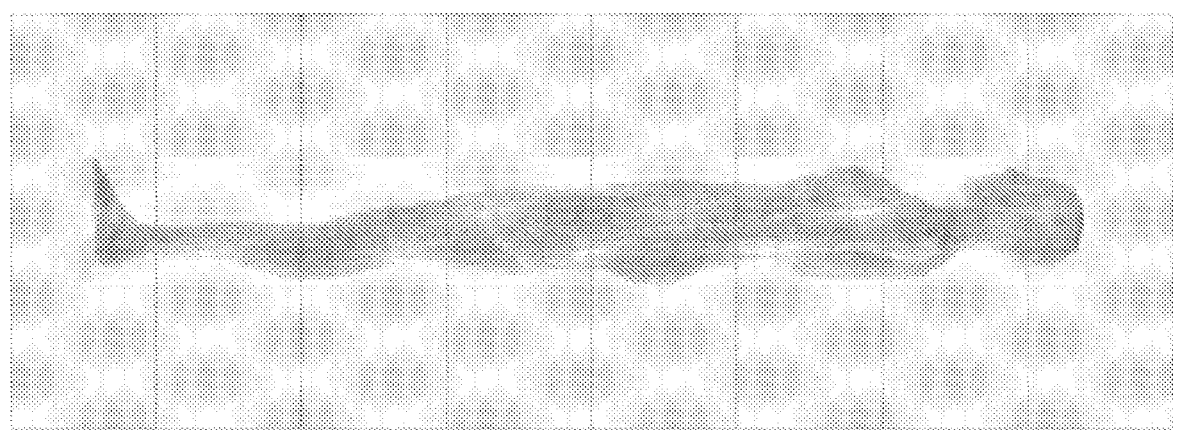
FIGS. 10-14 are schematic diagrams illustrating exemplary positional manners according to some embodiments of the present disclosure.

In some embodiments, as shown in FIG. 10, if a scanning range of a scanned object is from head to toe (i.e., the scanning range is the entire limb of the scanned object) and image quality from head to toe is required to be consistent or similar, a positional manner that centers the scanned object in a scanning region of a PET scanner may be adopted based on scanning parameters, that is, a target position of the scanned object in the scanning region is a position where the scanned object is placed in the middle of the entire scanning region.

Figure 11:
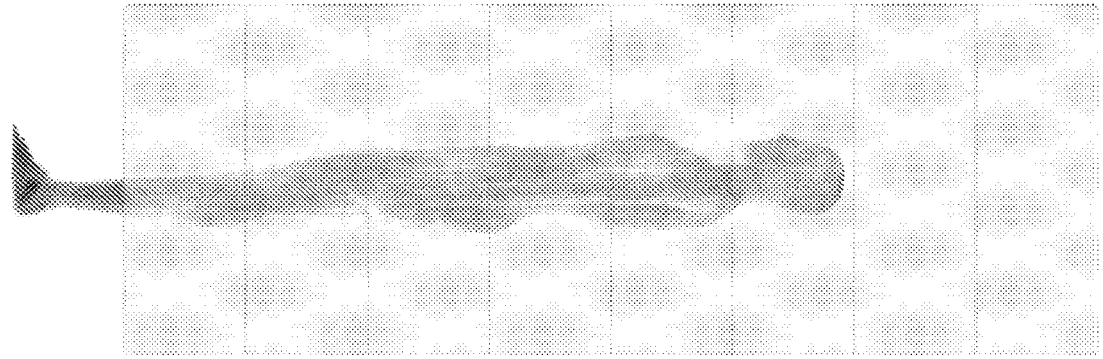

In some embodiments, as shown in FIG. 11, if a target scanned part of a scanned object is a head region and the scanned image is not required to completely cover a foot region and a leg region, according to scanning parameters, on the basis that a region from the head to the legs of the scanned object may be covered, the head region of the scanned object may be placed in a high-sensitivity subregion of the PET scanner closest to the head region by adopting a way that the head or feet enter the PET scanner first. For example, if a scanning region of the PET scanner is divided into eight sub-regions as shown in FIG. 9, and a positional manner of the scanned object is that the head faces a direction of an inlet of a scanning couch, a position of the head region of the scanned object may be a sixth sub-region of the scanning region.

Figure 12:
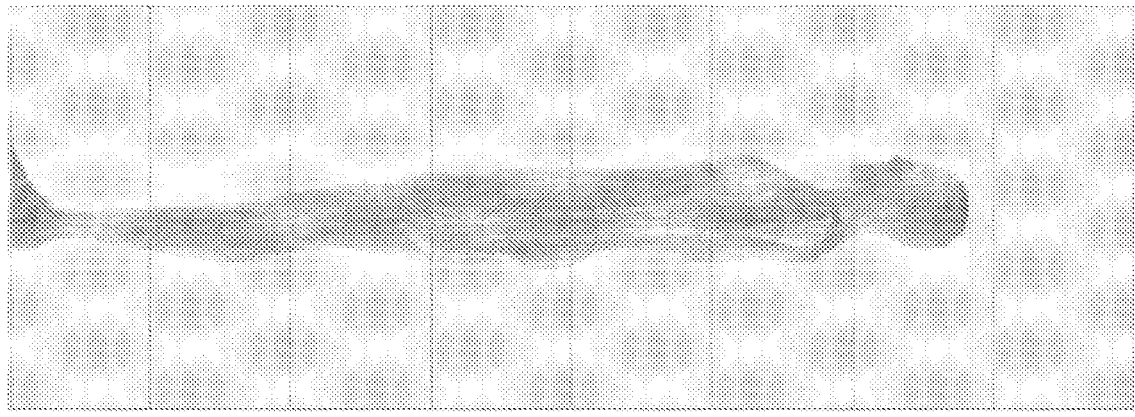

In some embodiments, as shown in FIG. 12, if a scanning range of a scanned object is from head to toe (i.e., the scanning range is the entire limb of the scanned object) and image quality of the head image is required to be higher, a positional manner that makes the sole of the scanned object flush with the edge of the scanning region may be adopted based on scanning parameters. For example, if a scanning region of the PET scanner is divided into eight sub-regions as shown in FIG. 9, the target position of the scanned object in the scanning region is a position where the sole of the scanned object is aligned with the edge of the first subregion when the positional manner of the scanned object is that the head of the scanned object towards a direction of an inlet of a scanning couch.

Figure 13:
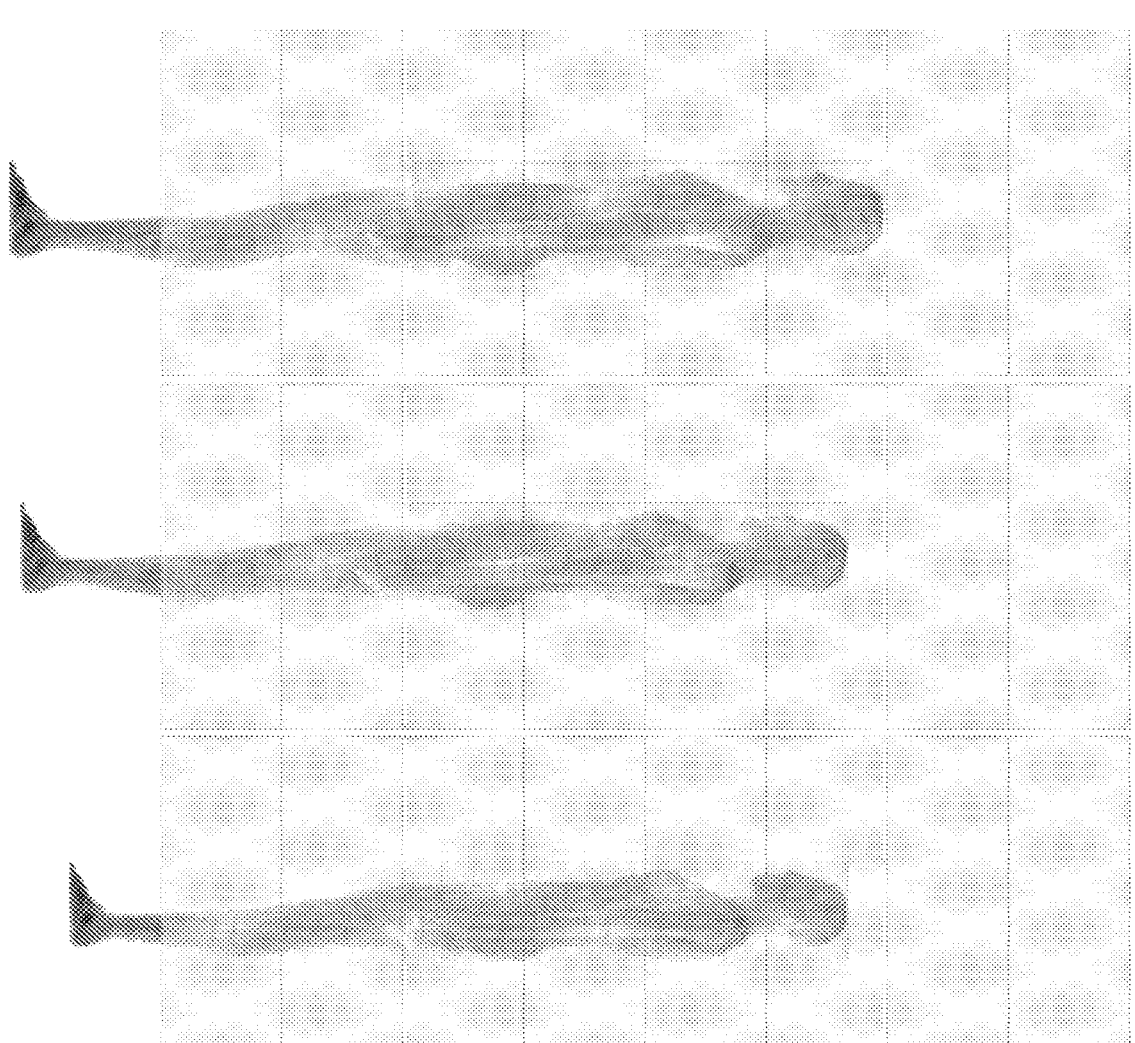

In some embodiments, as shown in FIG. 13, if a scanning range of a scanned object is from head to torso, image qualities of the head image and the torso image are required to be high, and there are no image quality requirements for the foot image and the lower leg image, a positional manner that centers the head and torso of the scanned object in a scanning region may be adopted. For example, if a scanning region of the PET scanner is divided into eight sub-regions as shown in FIG. 9, the head and torso of the scanned object may be positioned in a third sub-region, a fourth sub-region, a fifth sub-region, and a sixth sub-region with high sensitivity. For example, a top graph in FIG. 13 shows a position of a scanned object with a height of about 180 cm in a scanning region, a middle graph in FIG. 13 shows a position of a scanned object with a height of about 170 cm in the scanning region, and a bottom graph in FIG. 13 shows a position of a scanned object with a height of about 160 cm in the scanning region.

Figure 14:
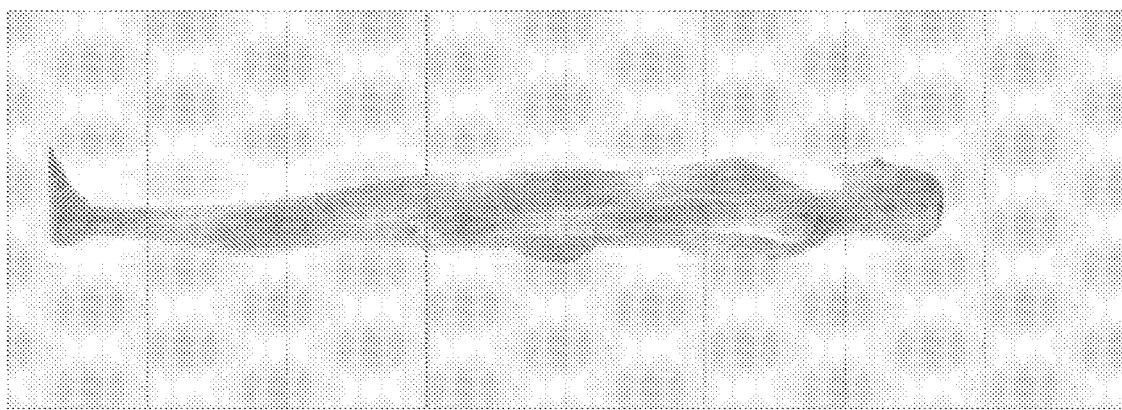

In some embodiments, as shown in FIG. 14, if a scanning range of a scanned object is from head to toe (i.e., the scanning range is the entire limb of the scanned object) and image quality from head to toe is required to be consistent or similar, a positional manner that centers a gravity point of the scanned object in a scanning region of a PET scanner may be adopted. For example, if the scanning region of the PET scanner is divided into eight sub-regions as shown in FIG. 9, a navel position (i.e., the gravity point) of the scanned object may be placed at a junction of the fourth sub-region and the fifth sub-region.

It should be noted that the operations illustrated in the process described above or in the flowchart of the accompanying drawings may be performed by a computer system including a set of computer-executable instructions. In addition, although the order of the operations is illustrated, in some cases, the operations may be performed in an order different from that shown herein.

FIG. 15 is a block diagram illustrating an exemplary image scanning device according to some embodiments of the present disclosure.

As shown in FIG. 15, in some embodiments, the image scanning device 1500 may include a data acquisition module 1510, a scanning parameter determination module 1520, a target position determination module 1530, a control module 1540, and a scanning module 1550. In some embodiments, the data acquisition module 1510 and the data acquisition unit 313 in the acquisition module 310 may have the same structure and/or function; the scanning parameter determination module 1520 and the scanning parameter determination unit 321 in the determination module 320 may have the same structure and/or function; the target position determination module 1530 and the target position determination unit 323 in the determination module 320 may have the same structure and/or function; and the control module 1540 and the control module 330 may have the same structure and/or function.

The data acquisition module 1510 may be configured to obtain information data of a scanned object. For example, the data acquisition module 1510 may be configured to obtain the information data such as identity information, medical information, positional information, and/or positioning image, etc., of the scanned object.

The scanning parameter determination module 1520 may be configured to determine scanning parameters. For example, the scanning parameter determination module 1520 may be configured to determine at least one scanning parameter based on the identity information, the medical information, the positional information, and/or the positioning image, etc., of the scanned object.

The target position determination module 1530 may be configured to determine a target position of the scanned object in a scanning region of a medical device based on the scanning parameters. In some embodiments, the target position determination module 1530 may be configured to determine the positional information based on the scanning parameters, determine scanning parameters of a scanning protocol in the medical device (e.g., a PET scanner) based on the positional information, and determine the target position of the scanned object in the scanning region of the medical device based on the scanning parameters of the scanning protocol. In some embodiments, the scanning parameters may correspond to one or more positional information. The positional information may be displayed in an interactive interface of the medical device (e.g., the PET scanner) in a form of a medical icon, a geometric figure, or a text list. In some embodiments, the target position determination module 1530 may be configured to determine the target position of the scanned object in the scanning region based on the positional information (and/or the scanning parameters) and an extent of divided sub-regions of the medical device (e.g., the PET scanner).

The control module 1540 may be configured to control a scanning couch to move the scanned object to the target position. In some embodiments, the control module 1540 may be configured to control a scanner to perform a scanning.

The scanning module 1550 may be configured to perform a scanning on the scanned object (e.g., a CT scanning, a PET scanning, etc.).

In some embodiments, the image scanning device 1500 may include an image acquisition module (not shown) configured to obtain a positioned image of the scanned object.

It should be noted that each of the above modules may be a functional module or a program module, which may be implemented by software or hardware. Each of the above modules implemented by hardware may be located in the same processor, or the above modules implemented by hardware may be located in different processors in any combination.

During scanning, the scanned object may be scanned again according to some other types of scanning protocols due to clinical diagnosis after partial scanning results have been obtained. For example, after a sagittal or coronal scanning of the spine, some abnormal lesions are found, and some information about the spine is wanted to be further scrutinized and a more detailed cross-sectional scanning of the intervertebral disc or vertebral body is desired. At this time, the scanning protocol corresponding to the cross-sectional position needs to be selected and added to the list for scanning. As another example, during a PET scanning, after a PET image is obtained, further research may be required on the medical findings in the image, thereby creating a need for further scanning of the medical finding.

In the prior art, after a scanning of a patient (i.e., a scanned object) is completed, a follow-up doctor needs to promptly confirm whether the patient has a lesion, and then confirm whether the patient needs to be scanned again. If the patient does not need to be scanned again, the scanning of the patient may be terminated. However, this method usually requires manual judgment by an experienced follow-up doctor, which has high labor costs and low efficiency.

The embodiments of the present disclosure provide an image scanning method for a medical device in which abnormal points in a scanned image may be automatically identified, a scanning protocol may be intelligently recommended based on the abnormal points, and a scanning may be performed on the scanned object according to the scanning protocol, which solves the problem of high labor costs and low efficiency in the process of abnormal points discovery or scanning confirmation in related technologies.

Figure 16:
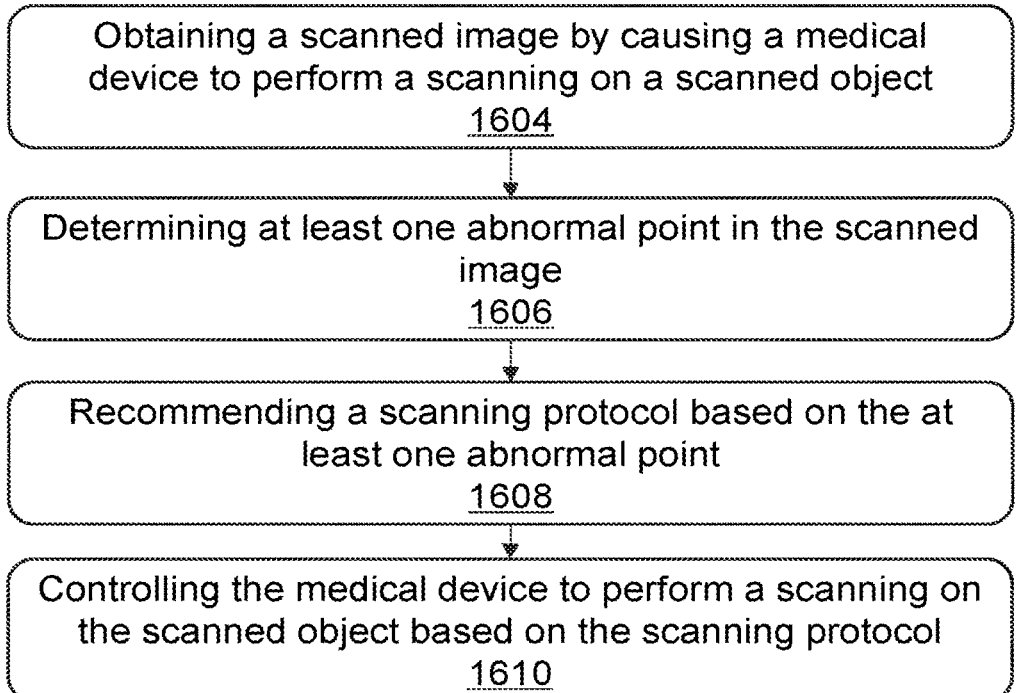
FIG. 16 is a flowchart illustrating an exemplary image scanning method according to some embodiments of the present disclosure.

FIG. 16 is a flowchart illustrating an exemplary image scanning method according to some embodiments of the present disclosure.

In some embodiments, the image scanning method 1600 may be executed by the image scanning system 100, the image scanning system 300, or an image scanning device 1700. For example, the image scanning method 1600 may be stored in a storage device (e.g., the storage device 150) in a form of programs or instructions, when executing the programs or instructions, the image scanning system 100 (e.g., the processing device 140) may implement the image scanning method 1600. The operations of the image scanning method 1600 presented below are intended to be illustrative. In some embodiments, the image scanning method 1600 may be accomplished with one or more additional operations not described and/or without one or more of the operations discussed. Additionally, the order of the operations of the image scanning method 1600 illustrated in FIG. 16 and described below is not intended to be limiting.

In 1604, a scanned image may be obtained by causing a medical device to perform a scanning on a scanned object. In some embodiments, operation 1604 may be performed by the processing device 140, the medical device 110, the acquisition module 310 (e.g., the image acquisition unit 313), or an image acquisition module 1720.

In some embodiments, the medical device in the operation 1604 may be a PET scanner, and accordingly, the obtained scanned image by performing the scanning on the scanned object may be a first PET scanned image. In some embodiments, the medical device (e.g., the PET scanner) may obtain a first PET scanning data of the scanned object by performing a PET scanning on the scanned object, and reconstruct the first PET scanned image of the scanned object based on the first PET scanning data.

In some embodiments, before the PET scanning is performed, a tomographic image including information of an anatomical structure of the scanned object may be obtained. The tomography image may show the tomographic structure of various parts of the scanned subject. In some embodiments, the tomography image may include a CT positioning image or an MRI positioning image, which is not limited in the embodiments. In some embodiments, the PET scanning may be performed in a scanning range corresponding to the tomography image of the scanned object to obtain the first PET scanning data of the scanned object, and the first PET scanned image corresponding to the tomography image of the scanned object is reconstructed based on the first PET scanning data.

In some embodiments, before the scanning of the scanned object is performed, a target position of the scanned object in a scanning region of the medical device may be determined. For example, scanning parameters may be determined based on information data and/or positioning image of the scanned object, and the target position of the scanned object in the scanning region of the medical device may be determined based on the scanning parameters. As another example, the target position of the scanned object in the scanning region of the medical device may be determined based on positional information and the scanning parameters. More descriptions regarding the determination of the target position of the scanned object in the scanning region of the medical device may be found elsewhere in the present disclosure (e.g., FIGS. 4-14 and the description thereof).

In 1606, at least one abnormal point in the scanned image may be determined. In some embodiments, operation 1606 may be performed by the processing device 140, the medical device 110, the determination module 320 (e.g., the abnormal point determination unit 325), or an identification module 1730.

In some embodiments, the at least one abnormal point in the obtained scanned image may be determined based on a machine learning model. In some embodiments, the at least one abnormal point in the scanned image may be intelligently identified and labeled. In some embodiments, the medical device may send the scanned image to a processing device, and the at least one abnormal point in the scanned image may be identified by a machine learning model that is trained by the processing device. The identification result may be sent to the medical device, and the medical device may perform a scanning based on the received identification result. It should be noted that, in some embodiments, other intelligent identification manners may be adopted to identify the abnormal points in the scanned image, which is not limited in the embodiments.

When the abnormal points in the scanned image are identified, the identified abnormal points may be labeled. For example, positions of glucose metabolism abnormal points in the first PET scanned image may be labeled using a box, a circle, or other irregular boundaries, and the manners of labeling the abnormal points are not limited in the embodiments. By labeling the abnormal points in the scanned image (e.g., the glucose metabolism abnormal points), the number and the positions of abnormal points in the scanned image may be clearly observed. After the abnormal points are added to labels, the number of the labels may be identified and recorded, and the scanning may be planned according to the number of the labels.

In some embodiments, the abnormal points in the scanned image may be identified in real time during an image reconstruction process. For example, when the scanned image is obtained by a short-axis PET scanner, the scanning needs to be performed multiple times, the abnormal points in each scanned image obtained in each scanning may be identified in real time during an image reconstruction process of the scanned image. In some embodiments, the abnormal points in the scanned image may be identified after the image reconstruction process is completed. In some embodiments, the at least one abnormal point in the scanned image may include at least one glucose metabolism abnormal point.

In 1608, a scanning protocol may be recommended based on the at least one abnormal point. In some embodiments, operation 1608 may be performed by the processing device 140, the medical device 110, the determination module 320 (e.g., the scanning protocol determination unit 327), or a recommendation module 1740.

In some embodiments, the scanning protocol corresponding to the abnormal point may be preset, and when the at least one abnormal point in the scanned image is identified, the corresponding scanning protocol is obtained and recommended to a user. In some embodiments, the recommended scanning protocol may be displayed on an interactive interface of the medical device (e.g., a PET-CT device) to prompt the user (e.g., a medical staff) to confirm the recommended scanning protocol. In some embodiments, the recommended scanning protocol may be displayed at a position of the abnormal point (e.g., the glucose metabolism abnormal point) in the scanned image (e.g., the first PET scanned image), and a display manner (e.g., enlarged display, highlighted display, etc.) of the recommended scanning protocol is not limited in the embodiments as long as it can guide the user to perform a next scanning step based on the abnormal point. In some embodiments, after the recommended scanning protocol is displayed on the interactive interface of the medical device, the user may be further prompted to confirm the scanning protocol by, for example, voice, ringing, message sending, vibration, etc.

In some embodiments, the user may confirm a scanning protocol to be performed from the recommended scanning protocol or a scanning protocol list. In some embodiments, if there is a deviation or shortage in the recommended scanning protocol, the user may manually modify the recommended scanning protocol. In some embodiments, scanning protocols to be recommended in the system may be updated based on the manual modification information of the user.

In 1610, the medical device may be controlled to perform a scanning on the scanned object based on the confirmed scanning protocol. In some embodiments, operation 1610 may be performed by the processing device 140, the medical device 110, the control module 330, or a scanning module 1750.

In some embodiments, after an instruction to confirm the scanning protocol is received from a user (e.g., the medical staff), the medical device may be controlled to automatically perform the scanning on the scanned object according to the confirmed scanning protocol. In some embodiments, the medical device may perform the scanning on the scanned object according to the confirmed scanning protocol to obtain scanning data of the scanned object, and reconstruct a corresponding scanned image based on the scanning data.

In some embodiments, the scanning in operation 1604 and operation 1610 may be the same modal scanning. For example, the medical devices in operation 1604 and operation 1610 may be PET scanners, and the PET scanner in operation 1604 may perform a first PET scanning on the scanned object to obtain a first PET scanned image, and the PET scanner in operation 1610 may perform a second PET scanning on the scanned object to obtain a second PET scanned image according to the confirmed scanning protocol. In some embodiments, scanning parameters of the first PET scanning and the second PET scanning may be the same or different. For example, a scanning range and position points within the scanning range in the first PET scanning may be the same as that in the second PET scanning. In some embodiments, the target position of the scanned object in the scanning region of the medical device may be determined based on the confirmed scanning protocol, and the scanning couch may be controlled to move the scanned object to the target position to perform the second PET scanning on the scanned object.

In some embodiments, the scanning in operation 1604 and operation 1610 may be different modal scanning. For example, in some embodiments, the medical device may include a first modal imaging device and a second modal imaging device. In operation 1604, the first modal imaging device may be controlled to perform a scanning on the scanned object to obtain a scanned image. In operation 1610, the second modal imaging device may be controlled to perform a scanning on the scanned object based on a confirmed scanning protocol. In some embodiments, the second modal imaging device may perform a second scanning on the scanned object based on information of the at least one abnormal point and information of at least one second abnormal point. In some embodiments, the at least one second abnormal point includes at least one pulmonary nodule abnormal point. In some embodiments, the at least one second abnormal point may be determined based on a tomographic image of the scanned object, for example, a CT positioning image (i.e., a first CT scanned image).

In some embodiments, the first modal imaging device may include a PET scanner, and the second modal imaging device may include a CT scanner. For example, the second modal imaging device may be controlled to perform a second scanning (e.g., a second CT scanning) on the scanned subject based on information of at least one glucose metabolism abnormal point in the first PET scanned image obtained by the first modal imaging device in operation 1604 and the information of the at least one second abnormal point (e.g., the lung nodule abnormal point) in the tomographic image (e.g., the first CT scanned image) of the scanned object to obtain second scanning data (e.g., second CT scanning data) of the scanned object, and a second scanned image (e.g., a second CT scanned image) may be obtained by reconstructing the second scanning data.

In some embodiments, the recommended scanning protocol that matches with the abnormal point information (e.g., the glucose metabolism abnormal point) may include a delayed scanning protocol (i.e., a PET scanning protocol), and/or a thin-layer scanning protocol (i.e., a CT scanning protocol).

In the embodiments, when the abnormal point (e.g., the glucose metabolism abnormal point) is detected in the scanned image (e.g., the first PET scanned image), the delayed scanning protocol may be recommended to perform a second scanning (e.g., a second PET scanning) on the scanned object to obtain a greater amount of data to identify a diagnostic result of the scanned image, thereby improving the accuracy of the diagnosis.

In the embodiments, after a tomographic image is obtained, the second abnormal point in the tomographic image may be determined, and then the thin-layer scanning protocol may be recommended based on the information of at least one second abnormal point and at least one abnormal point (e.g., the glucose metabolism abnormal point) in the scanned image. A second scanning (e.g., a second CT scanning) may be performed on the scanned object based on the recommended scanning protocol. Specifically, when the glucose metabolism abnormal point is detected in the first PET scanned image, the thin-layer scanning protocol may be recommended based on the glucose metabolism abnormal point and the second abnormal point in the tomographic image (e.g., a first CT scanned image), thereby obtaining a more comprehensive and accurate diagnostic result of the scanned object. The scanning protocol is recommended by combining the information of the abnormal point in the scanned image obtained in operation 1604 with the second abnormal point in the tomographic image (i.e., multimodal combination), and the scanning is performed on the scanned object, thereby improving the accuracy of the detection.

Due to a relatively high radiation dose of the thin-layer scanning, normal scanning is usually used for routine physical examinations. A reconstruction layer of the normal scanning is thicker, accordingly, lesions may be missed, thereby resulting in tiny nodules not being easily detected. The thin-layer CT scanning uses reorganized layer thickness technology or 3D reconstruction technology to make the layer thickness thinner, which can reach 3 mm or even 1 mm. Because of the thinner layer thickness, relatively small lesions or relatively small tissues and organs may be observed by the thin-layer CT scanning. A common thin-layer scanning protocol corresponds to the thin-layer scanning of small nodules in the lungs. The thin-layer scanning also may be applied to special parts, such as pituitary gland, orbit, inner ear, adrenal gland, etc.

The presence of the glucose metabolism abnormality point in the PET scanned image indicates that the scanned object has a lesion in the scanning region. In the embodiments, the user may be intelligently recommended to further scan the scanning region of the scanned object using the thin-layer scanning protocol based on the information of the glucose metabolism abnormal point and the information of the second abnormal point, which may display the morphology and density of the lesion in a clearer and more detailed manner. For example, for lung lesions, small nodules of 1-2 mm are easily missed. By adopting the lung thin-layer scanning protocol, the CT layer thickness may reach 0.5 mm, thus avoiding the situation of missing small nodules in the lung. In addition, the thin-layer scanning may show a relationship between a lesion and surrounding tissues in a more detailed manner, and show subtle imaging signs, thereby helping doctors to treat the disease.

In some embodiments, a scanning may be planned based on the number of labels of abnormal points in the scanned image. For example, the scanned object may be moved to cause one of the at least one abnormal point in the scanned image to coincide with a position corresponding to a scanning center of the medical device (e.g., the PET scanner).

For example, if the number of labels of abnormal points in the scanned image is 1, the scanned object may be moved to cause the abnormal point to coincide with the position corresponding to the scanning center of the PET scanner. Specifically, a position corresponding to the label of the abnormal point may be used as a center point of a scanning range, and the scanned object may be moved to cause the position of the abnormal point (the glucose metabolism abnormal point) corresponding to the label to coincide with the position of the scanning center of the medical device (e.g., the PET scanner), and the medical device may be controlled to scan the scanning range centered on the abnormal point.

In some embodiments, if there are a plurality of labels of abnormal points in the scanned image, the scanned object may be moved to cause one of the plurality of abnormal points to coincide with the position corresponding to the scanning center of the medical device (e.g., the PET scanner). In some embodiments, if there are the plurality of labels of abnormal points in the scanned image, axial coordinates of each label may be calculated, and the scanning range may be planned based on maximum and minimum values of the axial coordinates to make that the scanning range covers the plurality of abnormal points corresponding to the plurality of labels, accordingly a more comprehensive and accurate scanning result may be obtained.

In some embodiments, if there are a plurality of labels of abnormal points in the scanned image, the abnormal points corresponding to the plurality of labels may be scanned separately by changing a position of a scanning couch. In some embodiments, after the scanning range including the plurality of labels has been planned, the scanned object may be moved to cause the abnormal point corresponding to at least one of the maximum and minimum values of the axial coordinates of the labels to coincide with the position corresponding to a center of a scanning range corresponding to a position of the scanning couch. For example, if two glucose metabolism abnormal points are identified in the first PET scanned image, a position of a label corresponding to one of the two glucose metabolism abnormal points may be used as a starting point of the scanning, and a position of a label corresponding to the other of the two glucose metabolism abnormal points may be used as an ending point of the scanning. The starting point of the scanning may be coincided with the center of the PET scanner, and the PET scanner may be controlled to scan from the starting point to the ending point.

In some embodiments, if there are a plurality of labels of abnormal points in the scanned image, the axial coordinates of the plurality of labels may be calculated, and the scanned object may be moved to cause an average of the axial coordinates to coincide with a center position of a planned scanning range of the scanned object.

In some embodiments, if there are a plurality of labels of abnormal points in the scanned image, according to the distribution of the plurality of labels in the scanned image, the scanned object may be moved to cause a center position of a densely distributed region of the labels to coincide with a center position of a planned scanning range of the scanned object. In some embodiments, if there are a plurality of labels of abnormal points in the scanned image, a trained machine learning model may be used to determine a scanning range of the scanned object and the abnormal point corresponding to the center position of the scanning range.

In some embodiments, if there are a plurality of labels of abnormal points in the scanned image, a scanning protocol list corresponding to the abnormal points may be recommended. Specifically, a scanning protocol database may be established in advance. After the abnormal points are identified, the scanning protocols associated with the abnormal points (e.g., the glucose metabolism abnormal points) may be looked up in the scanning protocol database and displayed in a list on the interactive interface of the medical device (e.g., a PET-CT device) for the user to select and confirm. After finding a desired scanning protocol, the user may add it to a scanning list by clicking on it, and then continue to select other protocols to be scanned, or the user may double-click on the scanning protocol to perform the scanning directly, thus simplifying the scanning process.

In some embodiments, the scanning protocols in the scanning protocol database may carry corresponding keywords by which the associated scanning protocol may be quickly found.

In some embodiments, the scanning protocol list may be displayed in a form that the recommended scanning protocols obtained by the lookup are displayed one by one in the order of acquisition, or the recommended scanning protocols obtained by the lookup may be displayed in groups with the corresponding abnormal points. For example, the scanning protocols associated with different sites of glucose metabolism abnormal points may be displayed in different folders. The user may open different folders for confirmation according to the situation. The specific way of displaying the scanning protocol list may be set according to the actual situation, which is not limited in the embodiments.

In some embodiments, the method 1600 may further include obtaining the scanned image obtained in operation 1610 and identifying at least one third abnormal point in the scanned image. The third abnormal point corresponds to the second abnormal point. In the present disclosure, the corresponding abnormal points in the different scanned images refer to that the abnormal points in the different scanned images correspond the same (approximately) part of the same scanned object presented in the scanned images. In the present disclosure, the "approximately" means that a deviation from the situation (e.g., the same part) described is less than a threshold value. For example, the corresponding abnormal points in the different scanned images refer to a proportion of that abnormal points corresponding to the same part of the same scanned object is higher than 80%, 90%, 95%, or the like.

For example, the third abnormal point in the second scanned image (e.g., the second CT scanned image) may be determined, and output information may be determined based on the third abnormal point. In some embodiments, the output information may include information output to be read by a doctor or technologist. The second scanned image is obtained by performing a medical scanning on the scanned object based on a scanning protocol recommended through a multimodal combination, and the output information is determined based on the third abnormal point in the second scanned image. The doctor or technologist may use the output information as a basis for diagnosis, thereby improving the accuracy of the diagnosis. In some embodiments, the second abnormal point and/or the third abnormal point in the scanned image may be determined by an intelligent identification manner such as a machine learning model.

Usually, in order to improve the efficiency and accuracy of detection, after the medical scanning of the scanned object, whether the scanned object needs to be scanned again may be determined based on the scanning result. Taking a tertiary hospital as an example, if there are three medical devices*25 Case/set, 75 scanned images would be obtained daily. Each medical device is usually equipped with at most 2 doctors. If the 75 scanned images are identified and analyzed, the two doctors need to go back and forth between a scanning operation room and a report room about 37 times before they may confirm whether the scanned object corresponding to each scanned image needs to be scanned again, which has high labor costs and low efficiency. The scanning operation room refers to a room where the scanned object is scanned. The report room refers to a room where the doctor organizes and summarizes the scanning reports. The doctor needs to obtain the scanned images of the scanned object in the scanning operation room in order to diagnose and analyze the condition of the scanned object. After the analysis, the doctor needs to go to the report room to organize and record the inspection data of the corresponding scanned object.

The embodiments of the present disclosure provide an image scanning method for a medical device in which abnormal points (e.g., glucose metabolism abnormal points) in a scanned image (e.g., a PET scanned image) obtained by the medical device (e.g., a PET scanner) may be automatically determined, and a scanning protocol matching the information of the abnormal points may be intelligently recommended based on the information of the abnormal points. The user (e.g., a doctor) only needs to confirm the scanning protocol from the recommended scanning protocol, and does not need to manually analyze the scanned image to identify the abnormal points and determine whether the scanned object needs to be scanned again, which reduces the user's time to go back and forth between the scanning operation room and the report room, thus saving labor costs and improving the efficiency of the process of abnormal point discovery or scanning confirmation.

It should be noted that the operations illustrated in method 1600 or the flowchart in FIG. 16 may be performed by a computer system including a set of computer-executable instructions. In addition, although the order of the operations of the method 1600 or the flowchart in FIG. 16 is illustrated, in some cases, the operations may be performed in an order different from that shown herein.

Figure 17:
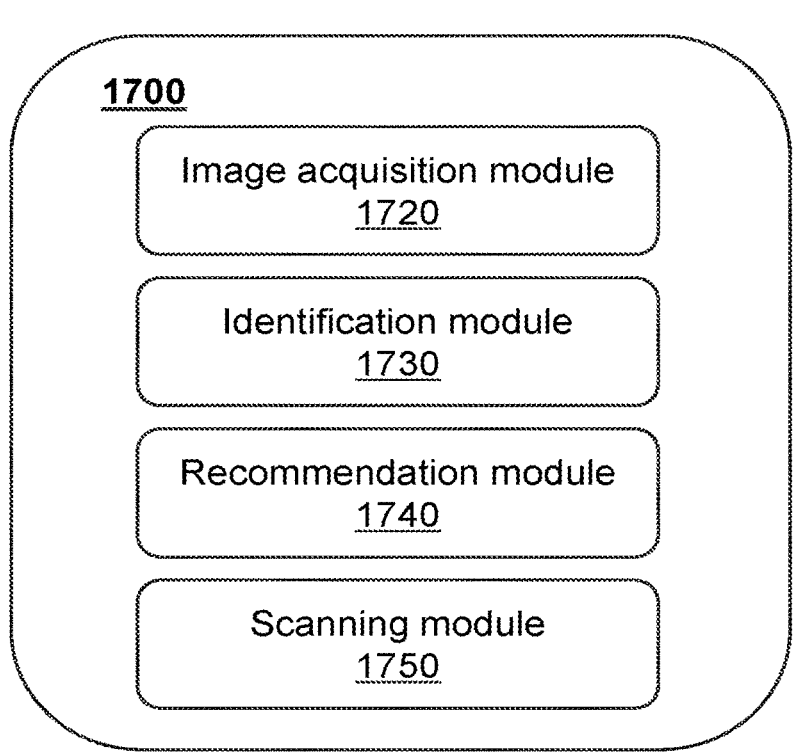
FIG. 17 is a block diagram illustrating an exemplary image scanning device according to some embodiments of the present disclosure.

FIG. 17 is a block diagram illustrating an exemplary image scanning device according to some embodiments of the present disclosure. In some embodiments, as shown in FIG. 17, the image scanning device 1700 may include an image acquisition module 1720, an identification module 1730, a recommendation module 1740, and a scanning module 1750. In some embodiments, the image acquisition module 1720 and the image acquisition unit 315 in the acquisition module 310 may have the same structure and/or function; the identification module 1730 and the abnormal point determination unit 325 in determination module 320 may have the same structure and/or function; the recommendation module 1740 and the scanning protocol determination unit 327 in the determination module 320 may have the same structure and/or function; and the scanning module 1750 and the control module 330 may have the same structure and/or function.

The image acquisition module 1720 may be configured to obtain a scanned image of a scanned object. For example, the image acquisition module 1720 may be configured to obtain a tomographic image including information of an anatomical structure of the scanned object. As another example, the image acquisition module 1720 may be configured to obtain a first PET image of the scanned object. In some embodiments, the image acquisition module 1720 may be configured to obtain scanning data of the scanned object, and reconstruct the scanned image of the scanned object based on the scanning data, for example, obtain the first PET scanned image by reconstructing the first PET scanning data of the scanned object.

The identification module 1730 may be configured to determine at least one abnormal point in the scanned image. For example, the identification module 1730 may be configured to intelligently identify the scanned image by a machine learning model to determine and label the at least one abnormal point in the scanned image. As another example, the determination module 320 may be configured to determine at least one second abnormal point in the tomographic image. As a further example, the determination module 320 may be configured to determine at least one corresponding abnormal point in different scanned images. In the present disclosure, the corresponding abnormal points in the different scanned images refer to that the abnormal points in the different scanned images correspond the same (approximately) part of the same scanned object presented in the scanned images. At least one third abnormal point corresponds to the at least one second abnormal point. In some embodiments, the identification module 1730 may be configured to determine output information based on the at least one third abnormal point in a second scanned image.

The recommendation module 1740 may be configured to recommend a scanning protocol based on information of the at least one abnormal point. In some embodiments, the recommendation module 1740 may be configured to display the recommended scanning protocol on an interactive interface of a medical device to prompt a user to confirm the scanning protocol.

The scanning module 1750 may be configured to perform a scanning on the scanned object according to the confirmed scanning protocol. For example, the scanning module 1750 may be configured to perform a second PET scanning on the scanned object based on the information of the at least one abnormal point to obtain scanning data of the scanned object, and reconstruct a scanned image based on the scanning data. As another example, the scanning module 1750 may be configured to perform a second CT scanning on the scanned object based on the information of the at least one abnormal point (e.g., the glucose metabolism abnormal point) and the tomographic image (e.g., a first CT scanned image) to obtain second CT scanning data of the scanned object, and obtain the second CT scanned image by reconstructing the second CT scanning data.

The image scanning device 1700 of the medical device provided in the embodiments of the present disclosure may obtain, by the image acquisition module 1720, scanning data (e.g., the first PET scanning data) of the scanned object, reconstruct, by the image acquisition module 1720, a scanned image (e.g., the first PET scanned image) based on the scanning data; identify, by the identification module 1730, at least one abnormal point (e.g., the glucose metabolism abnormal point) in the scanned image; recommend, by the recommendation module 1740, a scanning protocol based on the information of at least one abnormal point; and perform, the scanning module 1750, a scanning on the scanned object based on the scanning protocol. The above device 1700 automatically identifies at least one abnormal point in the scanned image and intelligently recommends a scanning protocol based on a position where there is an abnormal point, which solves the problem of high labor costs and low efficiency in the process of abnormal point discovery or scanning confirmation in related technologies.

For the specific limitations of the image scanning device 1700 of a medical device, refer to the above definition of the image scanning method 1600 of a medical device, which may not be repeated herein. The modules in the image scanning device 1700 of the medical device described above may be fully or partially implemented by software, hardware, and a combination thereof. The above modules may be embedded in or independent of a processor in a computer device in a form of hardware, and can also be stored in a memory of the computer device in a form of software, so that the processor may invoke and execute the corresponding operations of the above modules.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. In addition, some features, structures, or features in the present disclosure of one or more embodiments may be appropriately combined.

In addition, those skilled in the art can understand that various aspects of the present disclosure can be illustrated and described through several patentable categories or situations, including any new and useful processes, machines, products, or combinations of materials, or any new and useful improvements. Accordingly, all aspects of the present disclosure may be performed entirely by hardware, may be performed entirely by software (including firmware, resident software, microcode, etc.), or may be performed by a combination of hardware and software. The above hardware or software can be referred to as "data block", "module", "engine", "unit", "component" or "system". In addition, aspects of the present disclosure may appear as a computer product located in one or more computer-readable media, the product including computer-readable program code.

The computer storage medium may include a propagation data signal containing a computer program encoding, such as on a baseband or as part of a carrier. The propagation signal may have a variety of expressions, including electromagnetic form, optical form, or suitable combination form. The computer storage medium can be any computer readable medium other than the computer readable storage medium, which can be used to perform system, devices, or devices to implement communication, propagating, or devices by connecting to an instruction. Program encoding on a computer storage medium can be propagated by any suitable medium, including radio, cables, fiber optic cables, RF, or similar media, or any of the above media.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the program encoding may be run over the user's computer, or as a stand-alone package runs on the user's computer, or part is running on the user's computer, or running on a remote computer or processing device. In the latter case, the remote computer can be connected to the user's computer through any network, such as a local area network (LAN) or a wide area network (WAN), or connected to an external computer (e.g., via the Internet), or in a cloud computing environment, or as a service Use as software as a service (SaaS).

Furthermore, the recited order of processing elements or sequences, or the use of numbers, letters, or other designations thereof, are not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated.

Accordingly, in some embodiments, the numerical parameters set forth in the written description and attached claims are approximations that may vary depending upon the desired properties sought to be obtained by a particular embodiment. In some embodiments, the numerical parameters should be construed in light of the count of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable.

Each patent, patent application, patent application publication and other materials cited herein, such as articles, books, instructions, publications, documents, etc., are hereby incorporated by reference in their entirety. In addition to the application history documents that are inconsistent or conflicting with the contents of the present disclosure, the documents that may limit the widest range of the claim of the present disclosure (currently or later attached to this application) are excluded from the present disclosure. It should be noted that if the description, definition, and/or terms used in the appended application of the present disclosure is inconsistent or conflicting with the content described in the present disclosure, the use of the description, definition and/or terms of the present disclosure shall prevail.

At last, it should be understood that the embodiments described in the present disclosure are merely illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. An image scanning method for a medical device, the method being implemented on a computing device including at least one processor and at least one storage device, comprising:

dividing a scanning region into a plurality of sub-regions based on a sensitivity distribution and geometrical structure parameters of the scanning region;

determining a target position of a scanned object in the scanning region of the medical device based on information data of the scanned object and an extent of the plurality of sub-regions, wherein in response to that the scanned object is located at the target position, a target scanning site of the scanned object is located in the scanning region of the medical device;

moving the scanned object to the target position;

controlling the medical device to perform a first scanning on the scanned object to obtain a first scanned image of the scanned object;

determining at least one abnormal point in the first scanned image;

recommending a scanning protocol based on the at least one abnormal point; and controlling the medical device to perform a second scanning on the scanned object based on the scanning protocol.

2. The method of claim 1, wherein in response to that the scanned object is located at the target position, the target scanning site of the scanned object is located in a sub-region with a sensitivity higher than a preset threshold, and the preset threshold is determined based on a number of the plurality of divided sub-regions.

3. The method of claim 2, wherein the determining the target position of the scanned object in the scanning region of the medical device based on the information data of the scanned object and the extent of the sub-regions includes:

determining a scanning range of the scanned object based on the information data of the scanned object; and determining the target position from a range of the plurality of sub-regions based on the scanning range of the scanned object and image quality requirements of multiple regions within the scanning range in the first scanned image.

4. The method of claim 1, wherein the medical device includes a PET scanner, and the at least one abnormal point includes at least one glucose metabolism abnormal point.

5. The method of claim 1, wherein the determining the target position of the scanned object in the scanning region of the medical device includes:

determining a scanning range of the scanned object;

determining a geometric center of the scanning range; and determining the target position based on the geometric center of the scanning range and a center of the scanning region of the medical device.

6. The method of claim 1, wherein the medical device includes a first modal imaging device and a second modal imaging device, the first scanned image being obtained by the first modal imaging device;

the controlling the medical device to perform the second scanning on the scanned object based on the scanning protocol includes:

controlling the second modal imaging device to perform the second scanning on the scanned object based on the scanning protocol to obtain a second scanned image of the scanned object.

7. The method of claim 6, wherein the first modal imaging device includes a PET scanner, and the second modal imaging device includes a CT scanner.

8. The method of claim 1, wherein the recommending the scanning protocol based on the at least one abnormal point includes:

adding a label to each of the at least one abnormal point in the first scanned image; and recommending the scanning protocol based on a number of labels of the at least one abnormal point.

9. The method of claim 8, further comprising:

if the number of labels of the at least one abnormal point is 1, moving the scanned object to cause the abnormal point to coincide with a position corresponding to a scanning center of the medical device.

10. The method of claim 9, further comprising:

if there are a plurality of labels of abnormal points in the first scanned image, obtaining axial coordinates of each label of the plurality of labels, and planning a scanning range based on maximum and minimum values of the axial coordinates of the plurality of labels to make that the scanning range covers abnormal points corresponding to the plurality of labels.

11. The method of claim 10, further comprising:

if there are the plurality of labels of abnormal points in the first scanned image, moving the scanned object to cause a center position of a densely distributed region of the labels to coincide with a center position of the scanning range.

12. The method of claim 11, wherein the recommending the scanning protocol based on the at least one abnormal point includes:

if there are the plurality of labels of abnormal points in the first scanned image, looking up, in a scanning protocol database established in advance, scanning protocols associated with the abnormal points corresponding to the plurality of labels;

generating a scan protocol list corresponding to the abnormal points based on the scanning protocols; and displaying the scan protocol list on an interactive interface of the medical device.

13. An image scanning method for a medical device, the method being implemented on a computing device including at least one processor and at least one storage device, comprising:

dividing a scanning region into a plurality of sub-regions based on a sensitivity distribution and geometrical structure parameters of the scanning region; and determining a target position of a scanned object in the scanning region of the medical device based on information data of the scanned object and an extent of the plurality of sub-regions, wherein in response to that the scanned object is located at the target position, a target scanning site of the scanned object is located in the scanning region of the medical device;

controlling a scanning couch to move the scanned object to the target position; and controlling the medical device to perform a scanning on the scanned object.

14. The method of claim 13, further comprising:

determining scanning parameters, wherein the scanning parameters include at least one of a scanning range of the scanned object, position points within the scanning range, or a scanning duration; and determining, based on the scanning parameters, the target position of the scanned object in the scanning region of the medical device.

15. The method of claim 14, wherein the determining, based on the scanning parameters, the target position of the scanned object in the scanning region of the medical device includes:

obtaining positional information of the scanned object; and determining the target position of the scanned object in the medical device based on the positional information and the scanning parameters.

16. The method of claim 13, wherein the medical device includes a PET scanner, an axial length of the PET scanner being at least 0.75 m.

* * * * *